(12) United States Patent
Kubota et al.

(10) Patent No.: US 10,512,611 B2
(45) Date of Patent: Dec. 24, 2019

(54) MILLICAPSULE FORMULATIONS COMPRISING POLYUNSATURATED FREE FATTY ACIDS

(71) Applicant: Omthera Pharmaceuticals Inc., Wilmington, DE (US)

(72) Inventors: Hironori Kubota, Tokyo (JP); Etienne Thierry Charles Rogeau, Beinheim (FR); Tohru Amemiya, Shizuoka Pref. (JP); Julien Georges Meissonnier, Beinheim (FR); Anders Gillis Holmén, Molndal (SE); Andreas Rådevik, Molndal (SE); Hans Carlsson, Molndal (SE); Bengt Staffan Schantz, Molndal (SE)

(73) Assignee: Omthera Pharmaceuticals Inc., Wilmington, DE (US)

( * ) Notice: Subject to any disclaimer, the term of this patent is extended or adjusted under 35 U.S.C. 154(b) by 0 days.

(21) Appl. No.: 15/552,686

(22) PCT Filed: Feb. 19, 2016

(86) PCT No.: PCT/US2016/018571
§ 371 (c)(1),
(2) Date: Aug. 22, 2017

(87) PCT Pub. No.: WO2016/137825
PCT Pub. Date: Sep. 1, 2016

(65) Prior Publication Data
US 2018/0325829 A1  Nov. 15, 2018

(30) Foreign Application Priority Data
Feb. 23, 2015 (EP) .................................. 15305278

(51) Int. Cl.
| | | |
|---|---|---|
| *A61K 9/48* | (2006.01) | |
| *A61K 31/202* | (2006.01) | |
| *A61P 1/16* | (2006.01) | |
| *A61P 3/06* | (2006.01) | |
| *A61P 11/00* | (2006.01) | |
| *A61K 9/50* | (2006.01) | |
| *A61K 31/135* | (2006.01) | |

(52) U.S. Cl.
CPC .......... *A61K 9/4891* (2013.01); *A61K 9/4808* (2013.01); *A61K 9/4825* (2013.01); *A61K 9/4833* (2013.01); *A61K 31/202* (2013.01); *A61P 1/16* (2018.01); *A61P 3/06* (2018.01); *A61P 11/00* (2018.01); *A61K 9/5026* (2013.01); *A61K 9/5047* (2013.01); *A61K 9/5057* (2013.01); *A61K 31/135* (2013.01); *A61K 2300/00* (2013.01)

(58) Field of Classification Search
CPC .............. A61K 31/202; A61K 2300/00; A61K 9/4825; A61K 9/4833; A61K 31/135; A61K 31/196; A61K 35/60; A61K 9/4808; A61K 9/4816; A61K 9/485; A61K 9/4858; A61K 9/4866; A61K 9/4875; A61K 9/4891; A61K 9/5026; A61K 9/5047; A61K 9/5057; A23L 29/284; A23L 33/12; A23P 10/30; A61P 11/00; A61P 1/16; A61P 3/06

See application file for complete search history.

(56) References Cited

U.S. PATENT DOCUMENTS

| | | | | |
|---|---|---|---|---|
| 5,254,294 A | * | 10/1993 | Wunderlich | A61K 9/4833 264/4 |
| 5,686,106 A | * | 11/1997 | Kelm | A61K 9/4891 424/456 |
| 6,893,658 B1 | | 5/2005 | Ida et al. | |
| 8,282,961 B2 | | 10/2012 | Sin et al. | |
| 8,383,678 B2 | | 2/2013 | Sachetto et al. | |
| 9,050,308 B2 | | 6/2015 | Maines et al. | |
| 9,050,309 B2 | | 6/2015 | Maines et al. | |
| 2005/0197395 A1 | | 9/2005 | Jandacek et al. | |
| 2006/0165777 A1 | * | 7/2006 | Solomon | A61K 9/2072 424/451 |
| 2007/0184090 A1 | * | 8/2007 | Van Waterschoot | A61K 31/20 424/439 |
| 2009/0304784 A1 | | 12/2009 | Mane et al. | |

(Continued)

FOREIGN PATENT DOCUMENTS

| | | |
|---|---|---|
| EP | 2229939 A1 | 9/2010 |
| JP | S59-225115 A | 12/1984 |

(Continued)

OTHER PUBLICATIONS

International Search Report issued in corresponding International Patent Application No. PCT/US2016/018571 dated Apr. 29, 2016.

(Continued)

*Primary Examiner* — Mark V Stevens
(74) *Attorney, Agent, or Firm* — Morgan, Lewis & Bockius LLP

(57) ABSTRACT

Capsular dosage forms containing polyunsaturated fatty acid (PUFA) compositions are provided herein. In certain embodiments, unit dosage forms comprising a plurality of millicapsules containing a PUFA composition therein are provided as well as their methods of use and manufacture. In certain embodiments, capsular dosage forms are provided herein that include a unit dosage form comprising a plurality of millicapsules containing a polyunsaturated free fatty acid substantially in free acid form. In some embodiments, the PUFA composition is Epanova®.

22 Claims, 7 Drawing Sheets

(56) References Cited

U.S. PATENT DOCUMENTS

| | | |
|---|---|---|
| 2011/0097394 A1 | 4/2011 | Sachetto et al. |
| 2013/0108696 A1* | 5/2013 | Berge .................. A61K 9/1075 |
| | | 424/456 |
| 2013/0209556 A1* | 8/2013 | Maines ................ A61K 31/202 |
| | | 424/456 |
| 2013/0295173 A1 | 11/2013 | Machielse et al. |
| 2014/0348930 A1 | 11/2014 | Sancilio et al. |

FOREIGN PATENT DOCUMENTS

| | | |
|---|---|---|
| JP | S61-126016 A | 6/1986 |
| JP | H07-053356 A | 2/1995 |
| JP | 2009-520824 A | 5/2009 |
| JP | 2012-525338 A | 10/2012 |
| JP | 2015-503590 A | 2/2015 |
| WO | 96/36329 A1 | 11/1996 |
| WO | 2005/079853 A2 | 9/2005 |
| WO | 2007/066178 A2 | 6/2007 |
| WO | 2007/075841 A1 | 7/2007 |
| WO | 2008/020680 A1 | 2/2008 |
| WO | 2009/087938 A1 | 7/2009 |
| WO | 2010/124387 A1 | 11/2010 |
| WO | 2013/040507 A1 | 3/2013 |
| WO | 2013/059669 A1 | 4/2013 |
| WO | 2013/103902 A1 | 7/2013 |
| WO | 2013/169797 A1 | 11/2013 |
| WO | 2016/069446 A1 | 5/2016 |
| WO | 2016/073335 A1 | 5/2016 |
| WO | 2016/130417 A1 | 8/2016 |

OTHER PUBLICATIONS

International Preliminary Report on Patentability and Written Opinion issued in corresponding International Patent Application No. PCT/US2016/018571 dated Aug. 29, 2017.

Patient Information Pamphlet, EPANOVA (omega-3-carboxylic acids) Capsule, Highlights of Prescribing Information, XP055198006, May 1, 2014 (retrieved from the internet (http://www1.astrazeneca-us.com/pi/epanova.pdf)).

Extended European Search Report issued in corresponding European Patent Application No. 16756086.1 dated Nov. 15, 2018.

* cited by examiner

| COMPONENTS | PROCESS | IN-PROCESS CONTROLS |
|---|---|---|
| -Talc<br>-Titanium dioxide<br>-Iron oxide yellow<br>-Carboxymethylcellulose sodium<br>-Polysorbate 80<br>-Poly(ethyl acrylate, methyl acrylate) 2:1<br>-Water, purified | STAGE 7:<br>Capsule coating | |
| -Talc | STAGE 8:<br>Final mixing | |
| | STAGE 9:<br>Sachet filling | Fill Weight:<br>3070±153 mg<br>(Omefas capsules coat 1)<br>3180±159 mg<br>(Omefas capsules coat 2) |

FIGURE 2B

Part A: EPA, baseline adjusted mean plasma concentration vs time curves, administration under fasting conditions Part A: DHA, baseline adjusted mean plasma concentration vs time curves; administration under fasting conditions Baseline adjusted mean EPA plasma concentrations vs time curves; administration under fed conditions Baseline adjusted mean DHA plasma concentrations vs time curves; administration under fed conditions

MILLICAPSULE FORMULATIONS COMPRISING POLYUNSATURATED FREE FATTY ACIDS

CROSS-REFERENCE TO RELATED APPLICATIONS

This application is a U.S. National Stage application of International Application No. PCT/US2016/018571, filed on Feb. 19, 2016, said International Application No. PCT/US2016/018571 claims priority of European Application No. 15305278.2, filed Feb. 23, 2015. Each of the above listed applications is incorporated by reference herein in its entirety for all purposes.

BACKGROUND

In recent years, pharmaceutical compositions rich in omega-3 ("ω-3" or "n-3") polyunsaturated fatty acids ("PUFAs") have been developed to treat a variety of clinical indications. PUFA compositions are derived from natural sources, typically fish oils, and comprise one or more various species of omega-3 PUFAs, omega-6 PUFAs, and other minor components, including mono-unsaturated and saturated fatty acids. The PUFAs in these compositions typically exist either as the free fatty acid or in some other acid-derivatized form, such as ester form, particularly ethyl ester form.

Lovaza®, including its generic counterparts, is an FDA-approved pharmaceutical product for the treatment of severe hypertriglyceridemia and includes a PUFA composition comprising the omega-3 PUFA species eicosapentaenoic acid ("EPA") and docosahexaenoic acid ("DHA") in the form of ethyl esters in a weight ratio of about 46:38.

Vascepa® is another FDA-approved pharmaceutical product for the same clinical indication and includes a PUFA composition that is >96% pure EPA in the ethyl ester form, with substantially no DHA.

The nutraceutical product, OMAX3, sold as a dietary supplement and promoted in part to lower triglyceride levels, includes a PUFA composition that comprises EPA and DHA in a weight ratio of about 4.1:1, wherein the EPA and DHA are likewise in the ethyl ester form.

Epanova® (omega-3 carboxylic acids) is another FDA-approved product for the treatment of severe hypertriglyceridemia and includes a PUFA composition comprising EPA and DHA as well as the omega-3 PUFA species docosapentaenoic acid ("DPA"), all in substantially free acid form. Pharmacokinetic studies have demonstrated that EPA and DHA from the free fatty acid formulation in Epanova® are rapidly absorbed, and that absorption is less affected by dietary fat restriction compared with the ethyl ester formulation found in other commonly used omega-3 products. This is because, unlike the omega-3 acid ethyl ester formulations, there is no requirement of pancreatic lipase and carboxylester lipase for the digestion and absorption of Epanova®, enzymes that are produced when patients ingest a meal containing fat. Thus, there is an improved bioavailability of Epanova® under low-fat conditions, which offers a therapeutic advantage in patients with hypertriglyceridemia, who are advised to restrict their daily fat intake.

With the increasing availability and prescription of PUFA-based treatments—such as Lovaza®, Vascepa®, OMAX3, and Epanova®—there is a growing need for the formulation of PUFA compositions into capsular dosage forms that exhibit both therapeutic and commercial advantages.

The approved prescription capsular dosage forms of Epanova® contains 1 g of PUFA composition, resulting in a relatively large (25 mm length) capsule. In some patient populations or circumstances, such capsules may be difficult or inconvenient for patients to swallow, for example if administering to children, the elderly or infirm for whom swallowing is difficult (for example because of a previous stroke or other existing medical condition or because of traumatic injury), or such capsules may not be accepted because of personal preference. In such patient populations or circumstances, it would be convenient to have available a dosage form which could be more readily administered, so that the bioavailability advantages described above which are associated with Epanova® can be made available to all patients who might benefit.

Millicapsule formulations of PUFA compositions are known in the art, for example as commercialized as Lotriga™ and Epadel™ in Japan, both of which comprise approximately spherical millicapsules of 4 mm diameter. Both of these products contain PUFA compositions in ethyl ester form.

We have surprisingly found that it is possible to formulate the free fatty acid PUFA composition used in Epanova® into millicapsules and either:
  a) Mimic the bioavailability profile of Epanova® by using a relatively thin (as described hereinafter) coating of poly(ethylacrylate-methylmethacrylate) copolymer but with the potential advantages associated with the size of millicapsules described above; or
  b) Potentially reduce the dose of omega-3 fatty acids required to achieve certain lipid profile effects by using uncoated millicapsules.

For both cases a) and b), surprisingly the millicapsule formulations show potentially greater stability in respect of glyceride formation than the Epanova® 1 g capsule.

SUMMARY

In certain embodiments, capsular dosage forms are provided herein that include a unit dosage form comprising a plurality of millicapsules containing a polyunsaturated free fatty acid substantially in free acid form. In some embodiments, the PUFA composition is Epanova®.

In some embodiments, the unit dosage form comprises about 1500 mg to about 2500 mg of the PUFA composition, such as about 2000 mg of the PUFA composition. In other embodiments, the unit dosage form comprises about 500 mg to about 1500 mg of the PUFA composition, such as about 1000 mg of the PUFA composition.

In various embodiments, the unit dosage form comprises about 40 to about 200 millicapsules, such as about 80 millicapsules, which are soft gelatin capsules that comprise porcine Type A gelatin.

In some embodiments, the millicapsules of the unit dosage form are uncoated. In other embodiments, the millicapsules of the unit dosage form are coated, such as with a poly(ethylacrylate-methylmethacrylate) copolymer. In certain coated embodiments, the millicapsules have a weight ratio of PUFA composition to coating of about 10:1 to about 25:1. In other embodiments, the millicapsules have a weight ratio of PUFA composition to coating of about 25:1 to about 50:1.

In various embodiments, the millicapsules of the unit dosage form are approximately seamless. In some embodiments, the millicapsules of the unit dosage form are approximately spherical in shape and include a diameter, for example, from about 5 to about 3 mm, such as about 4 mm.

In certain embodiments, each millicapsule of the unit dosage form contains about 15 to about 50 mg of the PUFA composition, in particular about 25 mg of the PUFA composition.

In some embodiments, the unit dosage form is used in a method of treating severe hypertriglyceridemia comprising administering to a patient in need thereof the unit dosage form in an amount and for a duration sufficient to treat severe hypertriglyceridemia.

BRIEF DESCRIPTION OF THE FIGURES

FIGS. 2A-B provide an exemplary flow diagram of a manufacturing process for coated gelatin millicapsules according to a particular embodiment.

DETAILED DESCRIPTION

Figure 1:
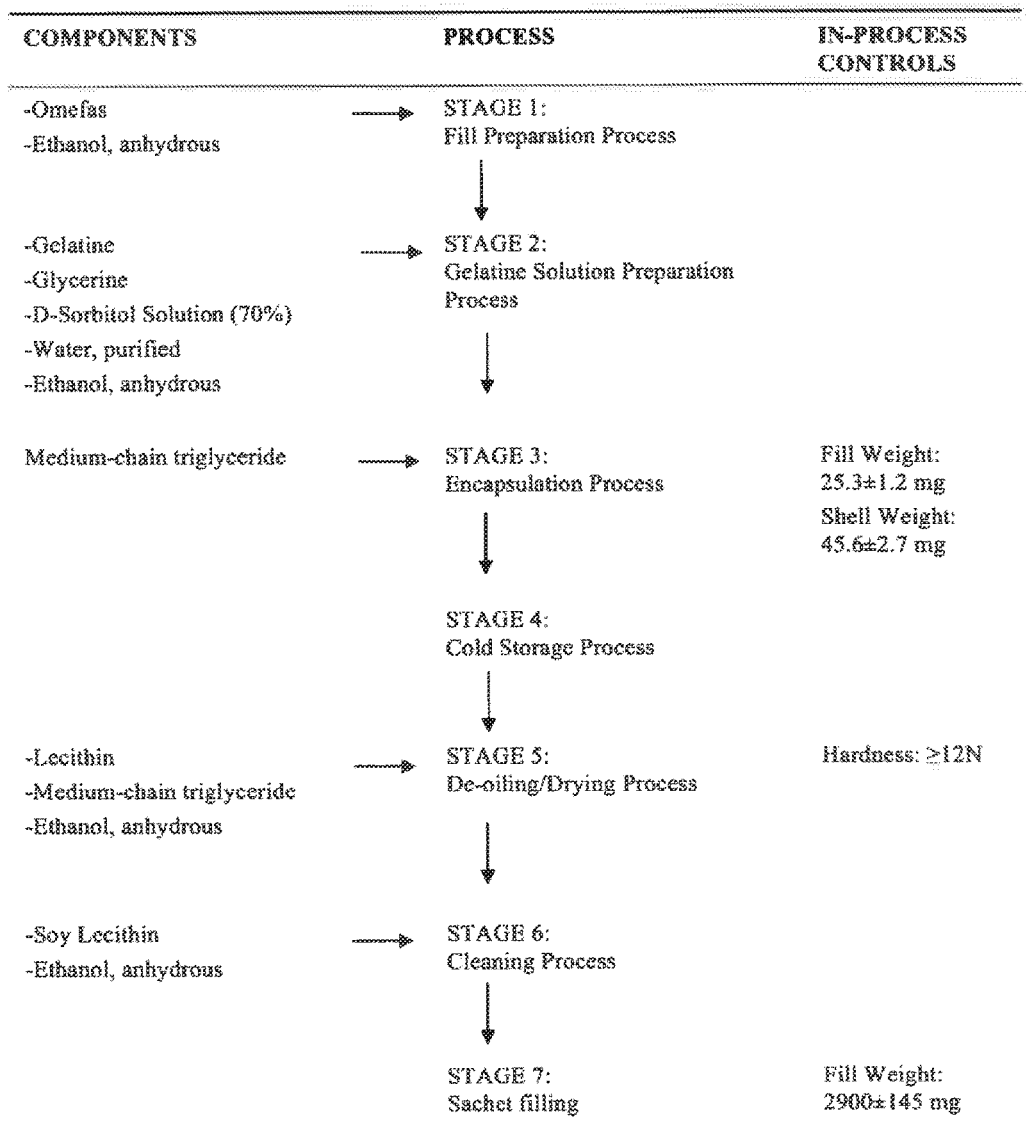
FIG. 1 provides an exemplary flow diagram of a manufacturing process for uncoated gelatin millicapsules according to a particular embodiment.

Millicapsule Formulations
Millicapsules

In certain embodiments, capsular dosage forms are provided herein which comprise a therapeutic PUFA composition within the capsule. In particular embodiments, the capsule is of millimeter dimensions, i.e., a "millicapsule." In some embodiments, capsular dosage forms herein comprise a plurality of millicapsules.

In various embodiments, millicapsules may be spherical or approximately spherical in shape and include a diameter from about 10 to about 0.1 mm, such as about 8 to about 0.5 mm, such as about 7 to about 1 mm, such as about 6 to about 2 mm, such as about 5 to about 3 mm, such as about 4 mm±about 0.1, 0.2, 0.3, or 0.5 mm. In some embodiments, the millicapsules include a diameter of about 1, 2, 3, 4, 5, 6, or 7 mm±about 0.1, 0.2, 0.3, or 0.5 mm.

In other embodiments, millicapsules are ellipsoidal or approximately ellipsoidal in shape and include semi-principle axes (i.e., semi-major axis and semi-minor axis of the corresponding ellipses) of millimeter dimensions. For example, millicapsules may be ellipsoidal in shape and include semi-principle axes independently selected from about 10 to about 0.1 mm, such as about 8 to about 0.5 mm, such as about 7 to about 1 mm, such as about 6 to about 2 mm, such as about 5 to about 3 mm, such as about 4 mm±about 0.1, 0.2, 0.3, or 0.5 mm. In some embodiments, the millicapsules include semi-principle axes independently selected from about 1, 2, 3, 4, 5, 6, or 7 mm±about 0.1, 0.2, 0.3, or 0.5 mm.

In certain embodiments where the millicapsules are ellipsoidal in shape, the millicapsules have a circular or approximately circular cross section (e.g., have two substantially equal semi-principle axes). In such embodiments, the diameter of the circular cross section may be selected from about 10 to about 0.1 mm, such as about 8 to about 0.5 mm, such as about 7 to about 1 mm, such as about 6 to about 2 mm, such as about 5 to about 3 mm, such as about 4 mm±about 0.1, 0.2, 0.3, or 0.5 mm. In some embodiments, the diameter of the circular cross section is about 1, 2, 3, 4, 5, 6, or 7 mm±about 0.1, 0.2, 0.3, or 0.5 mm.

In various embodiments, each millicapsule comprises a weight amount of the PUFA composition that varies by about 2, 5, 7, 10, 15, or 20% or less between millicapsules. For example, the millicapsule may include from about 5 to about 200 mg of the PUFA composition, such as from about 5 to about 150 mg, from about 7 to about 100 mg, from about 10 to about 75 mg, from about 15 to about 50 mg, from about 20 to about 30 mg, such as about 25 mg±about 1, 2, or 3 mg. In certain embodiments, the millicapsule includes about 5, 10, 15, 20, 25, 30, 40, 50, 75, or 100 mg±about 5 or 10% of the PUFA composition, in particular about 25 mg±about 5 or 10% of the PUFA composition.

In one embodiment, each millicapsule is spherical or approximately spherical in shape with a diameter of about 4 mm±about 0.1, 0.2, 0.3, or 0.5 mm, and includes about 25 mg±about 5 or 10% of the PUFA composition.

Millicapsule Unit Dosage Forms

In certain embodiments, unit dosage forms are provided herein that comprise a plurality of millicapsules. For example, in some embodiments, the unit dosage form comprises from about 5 to about 500 millicapsules, such as from about 10 to about 400 millicapsules, such as from about 20 to about 300 millicapsules, such as from about 40 to about 200 millicapsules, such as from about 60 to about 100 millicapsules, such as about 70 to about 90 millicapsules, such as about 80±about 2 or 5 millicapsules. In some embodiments, the unit dosage form comprises about 5, 10, 20, 30, 40, 50, 60, 70, 80, 90, 100, 110, 120, 130, 140, 150, or 200 millicapsules±about 2 or 5 millicapsules.

In some embodiments, the unit dosage form comprises from about 900 mg to about 4100 mg of the PUFA composition in a plurality of millicapsules, such as from about 1500 mg to about 3500 mg, including from about 1500 mg to about 3000 mg, 1500 mg to about 2500 mg, or from about 1900 mg to about 2100 mg. In some embodiments, the unit dosage form comprises about 1750, 1900, 2000, 2100, 2250, 2500, 3000, 3500, or 4000 mg±10, 20, 50, or 100 mg of the PUFA composition in a plurality of millicapsules. In particular embodiments, the unit dosage form comprises about 2000 mg±10, 20, 50, or 100 mg of the PUFA composition in a plurality of millicapsules. In certain embodiments, the unit dosage form comprises a non-integral weight amount of the PUFA composition between about 900 mg and 4100 mg in a plurality of millicapsules.

In various embodiments, the unit dosage form comprises from about 100 mg to about 2000 mg of the PUFA composition in a plurality of millicapsules, such as from about 500 mg to about 1500 mg, including from about 800 mg to about 1200 mg or from about 800 mg to about 1000 mg. In some embodiments, the unit dosage form comprises about 250, 500, 750, 900, 1000, or 1500 mg±10, 20, 50, or 100 mg of the PUFA composition in a plurality of millicapsules. In certain embodiments, the unit dosage form comprises a non-integral weight amount of the PUFA composition between about 100 mg and 2000 mg in a plurality of millicapsules.

In some embodiments, the unit dosage form comprises a plurality of millicapsules and has a total weight from about 800 mg to about 5000 mg, such as from about 1500 mg to about 4300 mg, such as from about 2000 mg to about 3800 mg, such as from about 2500 mg to about 3300 mg, such as from about 2700 mg to about 3100 mg, such as about 2900 mg±about 50, 100, 150, or 200 mg. In certain embodiments, the unit dosage form comprises a plurality of millicapsules and has a total weight of about 2000, 2500, 2700, 2800, 2900, 3000, 3100, 3500, or 4000 mg±about 50, 100, 150, or 200 mg.

In various embodiments, the unit dosage comprises a plurality of millicapsules and has a total weight from about 400 mg to about 2500 mg, such as from about 800 mg to about 2100 mg, such as from about 1000 mg to about 1900 mg, such as from about 1200 mg to about 1700 mg, such as from about 1300 mg to about 1600 mg, such as about 1450 mg±about 50, 100, 150, or 200 mg. In certain embodiments, the unit dosage form comprises a plurality of millicapsules and has a total weight of about 1000, 1200, 1300, 1400, 1450, 1500, 1600, 1700, or 2000 mg±about 25, 50, 100, or 150 mg.

In one embodiment, the unit dosage form comprises 80±1 to 5 millicapsules, wherein each millicapsule is spherical or approximately spherical in shape with a diameter of about 4 mm±about 0.1, 0.2, 0.3, or 0.5 mm and includes about 25 mg±about 5 or 10% of the PUFA composition.

Dosage Kits

In another aspect, a plurality of unit dosage forms as described above may be packaged together in a dosage kit to increase ease of use and patient compliance. In certain embodiments, the plurality of unit dosage forms is packaged as individual sachets, packets, stick-packs, or blisters in blister packs. A plurality of sachets, packets, stick-packs, or blister packs may optionally be packaged together in a box or other enclosure to provide the dosage kit. Typically, the dosage kit is sufficient for 30 days, 60 days, or 90 days of dosing. Thus, in selected embodiments, the unit dosage form comprises about 2000 mg of the PUFA composition as a plurality of millicapsules, and the dosage kit comprises 15, 30, 60, 90, 120, 150, 180, 240, 270, or 300 such unit dosage forms.

In various embodiments, the plurality of unit dosage forms is packaged under an inert gas, such as nitrogen or a noble gas, or is packaged under vacuum.

Millicapsule Materials

In particular embodiments, individual millicapsules include the PUFA composition as a liquid fill within the capsule.

In some embodiments, the millicapsule is a seamless or approximately seamless capsule, such as a seamless gelatin capsule, in particular a seamless soft gelatin capsule.

The millicapsule comprises porcine Type A gelatin. In some embodiments, the millicapsule comprises both Type A and Type B gelatin. Sources of collagen for the production of either Type A or Type B gelatin include, but are not limited to, cows, pigs, and fish.

In certain embodiments, the millicapsule is a soft gelatin capsule comprising a mixture of porcine Type A gelatin and a Type B gelatin. In various such embodiments, at least 1%, 2%, 3%, 4%, 5%, 10%, 15%, 20%, 25%, 30%, 40% even at least about 50% (w/w) of the gelatin is porcine Type A gelatin. In selected embodiments, at least about 55%, 60%, 65%, 70%, 75% (w/w) of the gelatin is porcine Type A gelatin. In particular embodiments, at least 80%, 85%, 90%, even 95% (w/w) of the gelatin is porcine Type A gelatin.

In various embodiments, the millicapsule is a soft gelatin capsule in which the gelatin consists essentially of porcine Type A gelatin.

In some embodiments, the gelatin is from about 100 to about 300 bloom, such as about 150 to about 250 bloom, such as about 200 bloom, such as 200 bloom±about 5 or 10%.

In certain embodiments, the millicapsule is a soft gelatin capsule in which the gelatin consists essentially of porcine Type A gelatin of 200 bloom±about 5 or 10%.

In one embodiment, the millicapsule is a seamless soft gelatin capsule in which the gelatin comprises porcine Type A gelatin, wherein the millicapsule is spherical or approximately spherical in shape with a diameter of about 4 mm±about 0.1, 0.2, 0.3, or 0.5 mm, and includes about 25 mg±about 5 or 10% of a PUFA composition.

In one embodiment, the millicapsule is a seamless soft gelatin capsule in which the gelatin comprises porcine Type A gelatin of 200 bloom±about 5 or 10%, wherein the millicapsule is spherical or approximately spherical in shape with a diameter of about 4 mm±about 0.1, 0.2, 0.3, or 0.5 mm, and includes about 25 mg±about 5 or 10% of a PUFA composition.

In one embodiment, the millicapsule is a seamless soft gelatin capsule in which the gelatin consists essentially of porcine Type A gelatin, wherein the millicapsule is spherical or approximately spherical in shape with a diameter of about 4 mm±about 0.1, 0.2, 0.3, or 0.5 mm, and includes about 25 mg±about 5 or 10% of a PUFA composition.

In one embodiment, the millicapsule is a seamless soft gelatin capsule in which the gelatin consists essentially of porcine Type A gelatin of 200 bloom±about 5 or 10%, wherein the millicapsule is spherical or approximately spherical in shape with a diameter of about 4 mm±about 0.1, 0.2, 0.3, or 0.5 mm, and includes about 25 mg±about 5 or 10% of a PUFA composition.

In various embodiments, the millicapsule is a gelatin capsule, such as those reported in U.S. Pat. Nos. 7,960,370 and 8,383,678, the contents of each of which are incorporated by reference herein in their entirety. In some embodiments, the millicapsule is a gelatin capsule and has a weight ratio of PUFA composition to gelatin of about 1:1 to about 5:1, such as about 1.5:1 to about 4:1, such as about 2:1 to about 3.5:1, such as about 2.5:1 to about 3:1, such as about 2.5:1 to about 2.8:1, such as about 2.6:1 or about 2.7:1, such as about 2.67:1±about 5 or 10%.

In certain embodiments, the millicapsule is a gelatin capsule, and the unit dosage form comprising a plurality of millicapsules includes about 250 to about 1250 mg of gelatin, such as about 500 to about 1000 mg, such as about 650 to about 850 mg, such as about 700 to about 800 mg, such as 750 mg±about 5 or 10%.

In certain embodiments, the millicapsule is a gelatin capsule and includes about 2 to about 30 mg of gelatin, such as about 5 to about 15 mg, such as about 7 to about 12 mg, such as about 8 to about 10 mg, such as 9 mg±about 0.1, 0.2, 0.3, or 0.5 mg.

In some embodiments, the millicapsule comprises one or more additional excipients, such as plasticizers, solvents, emulsifying agents, lubricants, dyes, colorants, flowing agents, anti-tacking agents, fillers, and manufacturing aids (e.g., medium-chain triglyceride).

In certain embodiments, the plasticizer is selected from glycerin (e.g., glycerin concentrate), sorbitol (e.g., D-Sorbitol), Triacetin, Macrogol, polyethylene glycols, propylene glycols, acetyl tributyl citrate, acetyl triethyl citrate, castor oil, acetylated monoglycerides, dibutyl sebacate, diethyl phthalate, tributyl citrate, and triethyl citrate. In some embodiments, the plasticizer is a mixture of glycerin and sorbitol.

In various embodiments, the solvent is selected from water, ethanol, n- or i-propanol, n- or i-butanol, ether, acetone, and mixtures thereof.

In some embodiments, the emulsifying agent is selected from lecithin (e.g., soy lecithin), polysorbate (e.g., polysorbate 80), Cremophor®, Kolliphor®, Kollisolv®, poloxamer, and cellulose ethers.

In certain embodiments, lubricants, flowing agents, and anti-tacking agents are selected from talc, corn starch, magnesium oxide, and magnesium or calcium stearate.

In various embodiments, fillers are selected from lactose, glucose, sucrose, starches and their hydrolysates, microcrystalline cellulose, sugar alcohols such as sorbitol or mannitol, and polysoluble calcium salts like calcium hydrogenphosphate and dicalcium- or tricalciumphosphate.

It will be understood that where the gelatin is described herein as consisting essentially of porcine Type A gelatin, this refers only to the gelatin content of the gelatin part of the capsule material such that other excipients and water and/or other solvents (such as ethanol) may also be present mixed with the gelatin.

In one embodiment, the millicapsule is a soft gelatin capsule in which the gelatin consists essentially of porcine Type A gelatin, and the gelatin is mixed with glycerol, sorbitol and water. In one embodiment, the millicapsule is a soft gelatin capsule in which the gelatin consists essentially of porcine Type A gelatin, and the gelatin is mixed with glycerol, sorbitol, ethanol and water.

In some embodiments, each millicapsule has an unfilled weight (i.e., not including the PUFA composition but including the capsule material and any excipients) that varies by about 2, 5, 7, 10, 15, or 20% or less between millicapsules. For example, the millicapsule may have an unfilled weight from about 5 to about 200 mg, such as from about 10 to about 150 mg, from about 20 to about 100 mg, from about 25 to about 75 mg, from about 35 to about 55 mg, from about 40 to about 50 mg, such as about 45 mg±about 1, 2, or 3 mg. In certain embodiments, the millicapsule has an unfilled weight of about 5, 10, 20, 30, 40, 45, 50, 60, 70, 80, or 100 mg±about 1, 2, 3, 4, or 5 mg, in particular about 45 mg±about 1, 2, 3, or 4 mg.

Millicapsule Coating

In certain embodiments, the millicapsule is uncoated.

In other embodiments, the millicapsule is coated with an active coat, for example, including a coating on the outside surface of the capsule. The term "active coat" as used herein means a coat which may have an effect on the release characteristics of the oil from the capsule. When a millicapsule is described herein as "coated" it should be understood to mean such an active coat is used. In any millicapsule embodiment or aspect herein, whether described as coated or uncoated, the skilled person will understand that a cosmetic (ie non-active or non-functional) coat may be applied to the millicapsule, for example to allow for imprinting of identifying marks or for colouration. Suitable examples of non-functional coats include polyvinylalcohol (PVA) based or PVA and hydroxypropyl methylcellulose (HPMC) based coatings such as Opadry amb II or Opadry II respectively (both supplied by Colorcon™).

In certain coated millicapsule embodiments, the coating permits the PUFA composition to be released in a time-dependent manner. In certain embodiments, when the millicapsules are coated with an amount of coating (such as a coating comprising a poly(ethylacrylate-methylmethacrylate) copolymer) such that the coating constitutes about 5% of the final millicapsule weight, between about 25% and 40% of the PUFA composition is released after 30 minutes as determined using United States Pharmacopeia/European Pharmacopeia dissolution apparatus II and quantitation of the released oil by HPLC and UV-detection at 216 nm, using an external standard. In certain embodiments, >70% of the PUFA composition is released after 360 minutes. These embodiments will be understood by the skilled person to refer to millicapsules which are ready for commercial sale, such that have had sufficient time after manufacture to dry and harden. For example in these embodiments, the millicapsules have been stored for at least 45 days, such as for at least 60 days, such as for at least 70 days, such as at least 75 days, such as at least 80 days after manufacture at 25° C. before being tested in the dissolution method. Suitably, the capsules are stored at 25° C. for 75 days before dissolution testing. Alternatively, as the skilled person will understand that the rate of drying and hardening of the gelatin and/or coating is temperature dependent, the millicapsules may be stored at higher temperatures for a shorter period of time.

In certain embodiments, when the millicapsules are coated with an amount of coating (such as a coating comprising a poly(ethylacrylate-methylmethacrylate) copolymer) such that the coating constitutes about 8% of the final millicapsule weight, between about 25% and 30% of the PUFA composition is released after 30 minutes as determined using United States Pharmacopeia/European Pharmacopeia dissolution apparatus II and quantitation of the released oil by HPLC and UV-detection at 216 nm, using an external standard. In certain embodiments, 50-60% of the PUFA composition is released after 240 minutes. Hardening of the capsules before testing is required as described immediately above.

In other embodiments, when the millicapsules are uncoated, substantially all of the PUFA composition is released within 10 mins, such as within 5 minutes, such as by 4 minutes when tested in using United States Pharmacopeia/European Pharmacopeia dissolution apparatus II and quantitation of the released oil by HPLC and UV-detection at 216 nm, using an external standard. After storage for 12 months at 25° C./60% Relative Humidity (RH) or 1 month storage at 40° C./75% RH in aluminium sachets, at least 80% of the PUFA composition is released after 30 minutes. The uncoated millicapsules should generally be stored in aluminum bags/sachets (at room temperature) to avoid contact with oxygen and moisture.

Surprisingly we have found that the presence or absence of a coating on the millicapsules has an effect on dissolution profile of the millicapsules after long term storage, with the uncoated capsules demonstrating some slowing of release rate over time (from initially very fast release, as shown above), and with the coated millicapsules showing less change in dissolution profile over up to 12 months storage at 25° C./60% RH in aluminium bags (for example the conditions used in the studies described in Example 4 hereinafter).

In one aspect there is provided a unit dosage form comprising a plurality of millicapsules containing a polyunsaturated free fatty acid (PUFA) composition substantially in free acid form, wherein the millicapsules are soft gelatin capsules comprising porcine Type A gelatin.

In certain embodiments, the millicapsule is coated as described in U.S. Pat. Nos. 5,792,795 and 5,948,818, the disclosures of which are incorporated herein by reference in their entireties. In various coated embodiments, the coating is a poly(ethylacrylate-methylmethacrylate) copolymer, such as poly(ethylacrylate-methylmethacrylate) 2:1. In some embodiments, the coating is Eudragit® NE 30 D (Evonik Industries AG). In other embodiments, the coating is another of the Eudragit®-type of coatings (Evonik Industries AG), such as a sustained release coating, such as Eudragit® RL 100, RL PO, RL 30 D, RL 12-5, RS100, RS PO, RS 30D, RS 12-5, NE 40 D, or NM 30 D. Suitably, the coating is NM30D. Reference herein to "NE30D" or "NM30D" will be understood to mean the Eudragit® NE30D or NM30D coatings respectively.

In various embodiments, the millicapsule coating includes one or more additional excipients, such as plasticizers, solvents, emulsifying agents, lubricants, dyes, colorants, flowing agents, anti-tacking agents, fillers, and manufacturing aids (e.g., medium-chain triglyceride), such as those described above for the millicapsule itself. It will be understood that one or more additional excipients may be provided as part of the commercial supply of polymer to be used. For example, Eudragit® NE30D contains nonylphenol ethoxylate as a surfactant and Eudragit® NM30D contains Brij®78P surfactant, the main component of which is polyethylene glycol octadecyl ether.

In some embodiments, the millicapsule coating includes a cellulose or cellulose ether, for example, as a viscosity enhancer. The cellulose ether may be selected from alkylcelluloses (such as methylcellulose and ethylcellulose), hydroxyalkylcelluloses (such as hydroxymethylcellulose, hydroxyethylcellulose, hydroxypropylcellulose, hydroxypropylmethylcellulose), carboxyalkylcelluloses (such as carboxymethylcellulose and carboxyethylcellulose), metal salts of carboxyalkylcelluloses (such as sodium carboxymethylcellulose and potassium carboxymethylcellulose), cellulose acetate phthalate (CAP), and hydroxypropylmethylcellulose phthalate. In certain embodiments, the millicapsule coating includes sodium carboxymethylcellulose.

In some embodiments, the millicapsule has a weight ratio of PUFA composition to coating of about 4:1 to about 100:1, such as about 5:1 to about 75:1, such as about 10:1 to about 50:1, such as about 10:1 to about 25:1, such as about 15:1 to about 20:1, such as about 18:1±about 5 or 10%. In other embodiments, the millicapsule has a weight ratio of PUFA composition to coating of about 10:1 to about 50:1, such as about 25:1 to about 50:1, such as about 30:1 to about 45:1, such as about 34:1 to about 40:1, such as about 38:1±about 5 or 10%.

In various embodiments, the millicapsule is a gelatin capsule, such as a soft gelatin capsule, and also includes a coating. In some such embodiments, the millicapsule has a weight ratio of gelatin to coating of about 2:1 to about 50:1, such as about 3:1 to about 25:1, such as about 4:1 to about 10:1, such as about 6:1 to about 8:1, such as about 7:1±about 5 or 10%. In other embodiments, the millicapsule has a weight ratio of gelatin to coating of about 2:1 to about 50:1, such as about 5:1 to about 25:1, such as about 10:1 to about 20:1, such as about 12:1 to about 17:1, such as about 14:1±about 5 or 10%.

In some coated embodiments, sufficient coating is applied such that the coating constitutes about 5% of the overall final weight of the millicapsules; for example, the coating constitutes 4.9% to 5.1%, or 4.8% to 5.2%, or 4.7% to 5.3%, or 4.6% to 5.4%, or 4.5% to 5.5% of the overall final weight of the millicapsules.

In other coated embodiments, sufficient coating is applied such that the coating constitutes about 8% of the overall final weight of the millicapsules.

Examples of suitable coatings are presented in Example 1 hereinafter. An example of a coating representing 5% of the overall weight of the capsules may contain carboxymethylcellulose sodium (1.6 mg), yellow iron oxide (1.0 mg), talc (90 mg), titanium dioxide (18 mg), polysorbate 80 (1.6 mg) and Eudragit® NM30D (52 mg) over 80 millicapsules, (made from a total of 2000 mg of PUFA composition and approximately 900 mg of gelatin mixture).

It will be appreciated that the above coating mixture contains insoluble solid material (such as talc) and will be applied to the millicapsules as a suspension. Where alternative polymers are used for the coating, or where the polymer is supplied with different surfactant (for example two different sources of poly(ethylacrylate-methylmethacrylate) 2:1), or variation in the other solid components are required (for example to achieve a different colour of the final product, or a thicker coat), adjustment of the amounts and/or types of excipients, in particular those with surfactant properties, may be required. It will be appreciated that for pharmaceutical use, the millicapsules must be reliably and reproducibly manufactured to meet a defined product specification. It is therefore important that the coating material remains as a suspension for a sufficient period and to a sufficient degree that these manufacturing criteria can be met. If the suspension starts to separate and form a sediment too soon or to too large a degree, the end product will not be uniformly coated.

Therefore in one aspect there is provided a stable solution suitable for coating porcine type A seamless millicapsules encapsulating a PUFA composition, wherein said stable solution comprises carboxymethylcellulose sodium, yellow iron oxide, talc, titanium dioxide, polysorbate 80 and Eudragit® NM30D, for example in a weight ratio of 1.6:1:90:18:1.6:52 respectively.

In a further aspect there is provided a process for coating porcine type A seamless millicapsules encapsulating a PUFA composition with a poly(ethylacrylate-methylmethacrylate) 2:1 containing coating comprising applying a solution comprising carboxymethylcellulose sodium, yellow iron oxide, talc, titanium dioxide, polysorbate 80 and Eudragit® NM30D, for example in a weight ratio of 1.6:1:90:18:1.6:52 respectively.

In one aspect, the millicapsule is a soft gelatin capsule, such as a soft porcine gelatin capsule, wherein the gelatin forms a layer with a thickness of 0.10 to 0.25 mm, such as 0.15 mm to 0.24 mm, such as 0.18 to 0.24 mm. In one embodiment of this aspect, the millicapsule further comprises a coating at a thickness of 0.03 to 0.05 mm, such as 0.032 to 0.048 mm, such as 0.032 to 0.046 mm, such as 0.034 to 0.042 mm, said coating comprising a poly(ethylacrylate-methylmethacrylate) copolymer, such as poly(ethylacrylate-methylmethacrylate) 2:1 (for example NM30D). In some embodiments of this aspect, the millicapsule is spherical or approximately spherical in shape with an overall diameter of about 4 mm±about 0.1, 0.2, 0.3, or 0.5 mm, and includes about 25 mg±about 5 or 10% of a PUFA composition as a liquid fill within the millicapsule.

In one embodiment, the millicapsule is a seamless soft gelatin capsule in which the gelatin consists essentially of porcine Type A gelatin of 200 bloom±about 5 or 10%, wherein the millicapsule is spherical or approximately spherical in shape with a diameter of about 4 mm±about 0.1, 0.2, 0.3, or 0.5 mm, and includes about 25 mg±about 5 or 10% of a PUFA composition as a liquid fill within the millicapsule, and wherein the millicapsule comprises about 5% by weight of a coating comprising poly(ethylacrylate-methylmethacrylate) 2:1 (such as Eudragit® NM30D).

In one embodiment, the millicapsule is a seamless soft gelatin capsule in which the gelatin comprises porcine Type A gelatin of 200 bloom±about 5 or 10%, wherein the millicapsule is spherical or approximately spherical in shape with a diameter of about 4 mm±about 0.1, 0.2, 0.3, or 0.5 mm, and includes about 25 mg±about 5 or 10% of a PUFA composition as a liquid fill within the millicapsule, and wherein the millicapsule comprises about 8% by weight of a coating comprising poly(ethylacrylate-methylmethacrylate) 2:1 (such as Eudragit® NM30D).

PUFA Compositions

In certain embodiments, capsular dosage forms are provided herein which comprise a therapeutic PUFA composition within the capsule. The PUFA composition includes PUFA species substantially in free acid form. The PUFA composition may include certain species of PUFAs, such as EPA, DHA, and DPA, either in various combinations or as individual species to the substantial exclusion of the others.

In certain embodiments, the PUFA composition comprises a plurality of species of omega-3 PUFAs, each present substantially in free acid form.

In certain aspects, the PUFA composition may comprise eicosapentaenoic acid (C20:5 n-3) ("EPA," also known as timnodonic acid), docosahexaenoic acid (C22:6 n-3) ("DHA," also known as cervonic acid), and docosapentaenoic acid (C22:5 n-3) ("DPA," also known as clupanodonic acid), each substantially in free acid form.

The phrase "substantially in free acid form," as used herein, refers to PUFAs in which at least 70% of the fatty acid is in the form of the free acid. For example, a composition comprising EPA, substantially in free acid form, means that at least 70% or more of the EPA molecules of the PUFA composition are in the form of the free acid. In a variety of embodiments, at least 80% or at least 90% of each of the plurality of species of omega-3 PUFA in the composition is in the free acid form. In certain embodiments, at least 91%, at least 92%, at least 93%, at least 94%, at least 95%, at least 96%, at least 97%, at least 98%, even at least 99% of each species of omega-3 PUFA in the composition is present in the free acid form. In exemplary embodiments, at least 90% of the total omega-3 PUFA content in the composition is present in the free acid form. In certain embodiments, at least 91%, at least 92%, at least 93%, at least 94%, at least 95%, at least 96%, at least 97%, at least 98%, even at least 99% of the total omega-3 PUFA content in the composition is present in the free acid form.

In various embodiments, at least 90% of each of the plurality of species of omega-6 PUFA in the PUFA composition is in the free acid form. In certain embodiments, at least 91%, at least 92%, at least 93%, at least 94%, at least 95%, at least 96%, at least 97%, at least 98%, even at least 99% of each species of omega-6 PUFA in the composition is present in the free acid form. In exemplary embodiments, at least 90% of the total omega-6 PUFA content in the composition is present in the free acid form.

In various embodiments, at least 90% of the total PUFAs in the PUFA composition are present in the free acid form. In certain embodiments, at least 91%, at least 92%, at least 93%, at least 94%, at least 95%, at least 96%, at least 97%, at least 98%, even at least 99% of the total PUFAs in the composition are present in the free acid form.

In certain embodiments, the PUFA composition comprises EPA, substantially in free acid form in a weight percent ("wt %") amount, relative to the total amount of fatty acids in the PUFA composition, of at least 45 wt %. In various embodiments, the PUFA composition comprises EPA, substantially in free acid form, in a weight percent amount of at least at least 46 wt %, at least 47 wt %, at least 48 wt %, at least 49 wt %, or at least 50 wt %. In certain embodiments, the PUFA composition comprises EPA, substantially in free acid form, in a weight percent amount of at least 51 wt %, at least 52 wt %, at least 53 wt %, at least 54 wt %, at least 55 wt %, at least 56 wt %, at least 57 wt %, at least 58 wt %, even at least 59 wt %, at least 60 wt %, at least 61 wt %, at least 62 wt %, at least 63 wt %, at least 64 wt %, or at least 65 wt %.

In various embodiments, the PUFA composition comprises EPA, substantially in free acid form, in a weight percent amount of 65 wt % or less, 62 wt % or less, 60 wt % or less, 59 wt % or less, 58 wt % or less, 57 wt %, or 56 wt % or less. In certain embodiments, the PUFA composition comprises EPA, substantially in free acid form, in a weight percent amount of 55 wt % or less, 54 wt % or less, 53 wt % or less, 52 wt % or less, 51 wt % or less, 50 wt % or less, 49 wt % or less, 48 wt % or less, 47 wt % or less or even 46 wt % or less. The PUFA compositions described herein include those in which the lower weight percent limits of EPA, described in the preceding paragraph, may be combined with any one of the upper limit weight percent described in this paragraph to form a range of EPA.

In various embodiments, the PUFA composition comprises EPA, substantially in free acid form, in an amount of about 50 wt % to about 60 wt %. In certain embodiments, EPA, substantially in free acid form, is present in an amount of about 52 wt % to about 58 wt %. In some embodiments, EPA, substantially in free acid form, is present in an amount of about 55 wt % to about 56 wt %. In certain embodiments, EPA, substantially in free acid form, is present in an amount of about 55 wt %.

In certain embodiments, the PUFA composition comprises DHA, substantially in free acid form, in an amount of at least 13 wt %. In various embodiments, the PUFA composition comprises DHA, substantially in free acid form, in an amount of at least 14 wt %, at least 15 wt %, at least 16 wt %, at least 17 wt %, at least 18 wt %, at least 19 wt %, or at least 20 wt %. In selected embodiments, the PUFA composition comprises DHA, substantially in free acid form, in an amount of at least 21 wt %, at least 22 wt %, at least 23 wt %, at least 24 wt %, even at least 25 wt %.

In various embodiments, the PUFA composition comprises DHA, substantially in free acid form, in a weight percent amount of 30 wt % or less, 27 wt % or less, 25 wt % or less, 24 wt % or less, 23 wt % or less, or 22 wt % or less. In certain embodiments, the PUFA composition comprises DHA, substantially in free acid form, in a weight percent amount of 21 wt % or less, 20 wt % or less, 19 wt % or less, 18 wt % or less, 17 wt % or less, or even 16 wt % or less. The PUFA compositions described herein include those in which the lower weight percent limits of DHA, described in the preceding paragraph, may be combined with any one of the upper limit weight percent described in this paragraph to form a range of DHA.

In various embodiments, the PUFA compositions comprise DHA, substantially in free acid form, in an amount of about 15 wt % to about 25 wt %. In certain embodiments, DHA, substantially in free acid form, is present in an amount of about 17 wt % to about 23 wt %. In certain embodiments, DHA, substantially in free acid form, is present in an amount of about 20 wt %.

In certain embodiments, the PUFA composition comprises DPA, substantially in free acid form, in an amount of at least 1 wt %. In various embodiments, the PUFA composition comprises DPA, substantially in free acid form, in an amount of at least 1.5 wt %, at least 2 wt %, at least 2.5 wt %, at least 3 wt %, at least 3.5 wt %, at least 4 wt %, at least 4.5 wt %, even at least 5 wt %. In selected embodiments, the PUFA composition comprises DPA, substantially in free acid form, in an amount of at least 6 wt %, at least 7 wt %, at least 8 wt %, or at least 9 wt %.

In various embodiments, the PUFA composition comprises DPA, substantially in free acid form, in a weight percent amount of 10 wt % or less, 8 wt % or less, 7 wt % or less, 6 wt % or less, 5 wt %, or 4 wt % or less, 3 wt % or less or even 2 wt % or less. The PUFA compositions described herein include those in which the lower weight percent limits of DPA, described in the preceding paragraph, may be combined with any one of the upper limit weight percent described in this paragraph to form a range of DPA.

In various embodiments, the PUFA composition comprises DPA, substantially in free acid form, in an amount of about 1 wt % to about 8 wt %. In particular embodiments, the PUFA composition comprises DPA, substantially in free acid form, in an amount of no more than about 10 wt %.

In certain embodiments, the PUFA composition comprises EPA and DHA, substantially in free acid form, in a total amount of at least 60 wt %. In various embodiments, the PUFA composition comprises EPA and DHA, substantially in free acid form, in a total amount of at least 61 wt %, at least 62 wt %, at least 63 wt %, at least 64 wt %, at least 65 wt %, at least 66 wt %, at least 67 wt %, at least 68 wt %, at least 69 wt %, or at least 70 wt %. In particular embodiments, the PUFA composition comprise EPA and DHA, substantially in free acid form, in a total amount of at least 71 wt %, at least 72 wt %, at least 73 wt %, at least 74 wt %, at least 75 wt %, at least 76 wt %, at least 77 wt %, at least 78 wt %, at least 79 wt %, even at least 80 wt %. In certain embodiments, the PUFA composition comprises EPA and DHA, substantially in free acid form, in total amount of at least 81 wt %, at least 82 wt %, at least 83 wt %, at least 84 wt %, even at least 85 wt %.

In various embodiments, the PUFA composition comprises EPA and DHA, substantially in free acid form, in a weight percent amount of 80 wt % or less, 79 wt % or less, 78 wt % or less, 77 wt %, or 76 wt % or less. In certain embodiments, the PUFA composition comprises EPA and DHA, substantially in free acid form, in a weight percent amount of 75 wt % or less, 74 wt % or less, 73 wt % or less, 72 wt % or less, 71 wt % or less, 70 wt % or less, 69 wt % or less, 68 wt % or less, 67 wt % or less, 66 wt % or less, 65 wt % or less, 64 wt % or less, 63 wt % or less, or even 62 wt % or less. The PUFA compositions described herein include those in which the lower weight percent limits of EPA and DHA, described in the preceding paragraph, may be combined with any one of the upper limit weight percent described in this paragraph to form a range of EPA and DHA.

In various embodiments, the PUFA composition comprises EPA and DHA, substantially in free acid form, in an amount of about 70 wt % to about 80 wt %. In certain embodiments, the PUFA composition comprises about 75 wt % EPA and DHA, substantially in free acid form.

In certain embodiments, the PUFA composition comprises EPA, DHA, and DPA, substantially in free acid form, in a total amount of at least 61 wt %. In typical embodiments, the PUFA composition comprises EPA, DHA, and DPA, substantially in free acid form, in a total amount of at least 62 wt %, at least 63 wt %, at least 64 wt %, at least 65 wt %, at least 66 wt %, at least 67 wt %, at least 68 wt %, at least 69 wt %, or at least 70 wt %. In certain embodiments, the PUFA composition comprises EPA, DHA, and DPA, substantially in free acid form, in a total amount of at least 71 wt %, at least 72 wt %, at least 73 wt %, at least 74 wt %, at least 75 wt %, at least 76 wt %, at least 77 wt %, at least 78 wt %, at least 79 wt %, at least 80 wt %, even at least 81 wt %, at least 82 wt %, at least 83 wt %, at least 84 wt %, at least 85 wt %, at least 86 wt %, at least 87 wt %, even at least 88 wt %.

In various embodiments, the PUFA composition comprises EPA, DHA, and DPA, substantially in free acid form, in a weight percent amount of 95 wt % or less, 94 wt % or less, 93 wt % or less, 92 wt %, or 91 wt % or less. In certain embodiments, the PUFA composition comprises EPA, DHA, and DPA, substantially in free acid form, in a weight percent amount of 90 wt % or less, 89 wt % or less, 88 wt % or less, 87 wt % or less, 86 wt % or less, 85 wt % or less, 84 wt % or less, 83 wt % or less, 82 wt % or less, 81 wt % or less, 80 wt % or less, 79 wt % or less, 78 wt % or less, or even 77 wt % or less. The PUFA compositions described herein include those in which the lower weight percent limits of EPA, DHA, and DPA, described in the preceding paragraph, may be combined with any one of the upper limit weight percent described in this paragraph to form a range of EPA, DHA, and DPA.

In a particular series of embodiments, the PUFA composition comprises EPA, substantially in free acid form, in an amount of about 55 wt % to about 56 wt %; DHA, substantially in free acid form, in an amount of about 19 wt % to about 20 wt %; and DPA, substantially in free acid form, in an amount of about 4 wt % to about 5 wt %.

In particular embodiments, the PUFA composition comprises EPA, substantially in free acid form, in an amount at least 50 wt %, DHA, substantially in free acid form, in an amount of at least 15 wt % and DPA, substantially in free acid form, in an amount of at least 1 wt %.

In particular embodiments, the PUFA composition comprises EPA, substantially in free acid form, in an amount of 50 wt % to 60 wt %, DHA, substantially in free acid form, in an amount of 15 wt % to 25 wt % and DPA, substantially in free acid form, in an amount of 1 wt % to 8 wt %.

In particular embodiments, the PUFA composition comprises EPA, substantially in free acid form, in an amount of 50 wt % to 60 wt %, DHA, substantially in free acid form, in an amount of 17 wt % to 23 wt % and DPA, substantially in free acid form, in an amount of 1 wt % to 8 wt %. In particular embodiments, the PUFA composition is that used in Epanova® or a generic form thereof. In further particular embodiments, the PUFA composition comprises EPA, substantially in free acid form, in an amount of 50 wt % to 60 wt %, DHA, substantially in free acid form, in an amount of 17 wt % to 23 wt % and DPA, substantially in free acid form, in an amount of 1 wt % to 8 wt %, wherein at least 90% by weight of the polyunsaturated fatty acid in the composition is present in the free acid form.

In some embodiments, the weight percent amounts of PUFAs may be measured or approximated as a percentage by area ("a/a") on a GC chromatogram of all fatty acids in the PUFA composition.

In certain embodiments, the PUFA composition further comprises one or more omega-3 PUFA species selected from the group consisting of: α-linolenic acid (C18:3 n-3), moroctic acid (C18:4 n-3, also known as stearidonic acid), eicosatrienoic acid (C20:3 n-3), eicosatetraenoic acid (C20:4 n-3), and heneicosapentaenoic acid (C21:5 n-3). In particular embodiments, the PUFA composition comprises EPA, DHA, DPA, and moroctic acid, each substantially in the free acid form. In a variety of embodiments, the PUFA composition comprises EPA, DHA, DPA, moroctic acid, and heneicosapentaenoic acid, each substantially in the free acid form. In specific embodiments, the PUFA composition comprises EPA, DHA, DPA, moroctic acid, heneicosapentaenoic acid, and eicosatetraenoic acid, each substantially in the free acid form. In selected embodiments, the PUFA composition comprises EPA, DHA, DPA, α-linolenic acid (C18:3 n-3), moroctic acid (C18:4 n-3), eicosatrienoic acid (C20:3 n-3), eicosatetraenoic acid (C20:4 n-3), and heneicosapentaenoic acid (C21:5 n-3).

In various embodiments, total omega-3 fatty acids—defined as the sum of alpha-linolenic acid (C18:3 n-3), moroctic acid (C18:4 n-3), eicosatrienoic acid (C20:3 n-3), eicosatetraenoic acid (C20:4 n-3), eicosapentaenoic acid (EPA) (C20:5 n-3), heneicosapentaenoic acid (C21:5 n-3), docosapentaenoic acid (C22:5 n-3) and docosahexaenoic acid (DHA) (C22:6 n-3)—constitute from about 80 wt % to about 95 wt % of all fatty acids in the PUFA composition.

In various embodiments, the PUFA composition further comprises one or more species of omega-6 PUFA, each present substantially in the free acid form.

In certain embodiments, the PUFA composition comprises one or more species of omega-6 PUFA selected from the group consisting of linoleic acid (C18:2 n-6), gamma-linolenic acid (C18:3 n-6), eicosadienoic acid (C20:2 n-6), dihomo-gamma-linolenic acid (C20:3 n-6) ("DGLA"), arachidonic acid (C20:4 n-6) ("AA"), and docosapentaenoic acid (C22:5 n-6, also known as osbond acid).

In particular embodiments, the PUFA composition comprises linoleic acid (C18:2 n-6), gamma-linolenic acid (C18:3 n-6), eicosadienoic acid (C20:2 n-6), dihomo-gamma-linolenic acid (C20:3 n-6) ("DGLA"), arachidonic acid (C20:4 n-6) ("AA"), and docosapentaenoic acid (C22:5 n-6), each present substantially in the ester (e.g., ethyl ester) or free acid form.

In certain embodiments, AA is present in an amount of no more than about 5 wt % of the fatty acids in the PUFA composition. In certain embodiments, AA comprises no more than about 4.5 wt % of the fatty acids in the PUFA composition. In particular embodiments, AA is present in an amount of no more than about 4 wt % of the fatty acids in the PUFA composition.

In certain embodiments, total omega-6 polyunsaturated fatty acids—defined as the sum of linoleic acid (C18:2 n-6), gamma-linolenic acid (C18:3 n-6), eicosadienoic acid (C20:2 n-6), dihomo-gamma-linolenic acid (C20:3 n-6), arachidonic acid (C20:4 n-6) and docosapentaenoic acid (C22:5 n-6)—comprise no more than about 10 wt % of the fatty acids in the PUFA composition.

In certain embodiments, PUFAs other than omega-3 and omega-6 PUFAs are present in an amount of no more than about 5 wt %.

In some embodiments, the PUFA composition comprises no more than about 3 wt % saturated fatty acids and no more than about 5 wt % mono-unsaturated fatty acids.

In various embodiments, the PUFA composition further comprises an antioxidant. In certain embodiments, the antioxidant is butylated hydroxyanisole (BHA). In some embodiments, the antioxidant is alpha-tocopherol.

In some embodiments, the PUFA composition is that used in Epanova®. Suitable examples of PUFA compositions that maybe used with the capsular dosage forms herein include those disclosed in U.S. Published Patent Application Nos. 2013/0177643 and 2013/0209556, the contents of each of which are incorporated by reference herein in their entirety.

In particular embodiments, unit dosage forms are provided herein that comprise about 2000 mg±10, 20, 50, or 100 mg of the PUFA composition of Epanova® in a plurality of millicapsules, such as in about 80±about 2 or 5 millicapsules, wherein the millicapsules are soft gelatin capsules comprised of Type A gelatin. In some of such embodiments, the millicapsules are uncoated. In other of such embodiments, the millicapsules are coated, such as with a poly(ethylacrylate-methylmethacrylate) copolymer, such as poly(ethylacrylate-methylmethacrylate 2:1. In particular embodiments the unit dosage forms are sachets, such as aluminum sachets.

In particular embodiments, the millicapsule is a spherical or approximately spherical soft porcine gelatin capsule with an overall diameter of about 4 mm±about 0.1, 0.2, 0.3, or 0.5 mm; wherein the gelatin forms a layer with a thickness of 0.10 to 0.25 mm, such as 0.15 mm to 0.24 mm, such as 0.18 to 0.24 mm; and wherein the gelatin layer encapsulates about 25 mg±about 5 or 10% of a PUFA composition comprising EPA, substantially in free acid form, in an amount of 50 wt % to 60 wt %, DHA, substantially in free acid form, in an amount of 15 wt % to 25 wt % and DPA, substantially in free acid form, in an amount of 1 wt % to 8 wt %.

In particular embodiments, the millicapsule is a spherical or approximately spherical soft porcine gelatin capsule with an overall diameter of about 4 mm±about 0.1, 0.2, 0.3, or 0.5 mm; wherein the gelatin forms a layer with a thickness of 0.10 to 0.25 mm, such as 0.15 mm to 0.24 mm, such as 0.18 to 0.24 mm; wherein the gelatin layer encapsulates about 25 mg±about 5 or 10% of a PUFA composition comprising EPA, substantially in free acid form, in an amount of 50 wt % to 60 wt %, DHA, substantially in free acid form, in an amount of 17 wt % to 23 wt % and DPA, substantially in free acid form, in an amount of 1 wt % to 8 wt %.

In particular embodiments, the millicapsule is a spherical or approximately spherical soft porcine gelatin capsule with an overall diameter of about 4 mm±about 0.1, 0.2, 0.3, or 0.5 mm; wherein the gelatin forms a layer with a thickness of 0.10 to 0.25 mm, such as 0.15 mm to 0.24 mm, such as 0.18 to 0.24 mm; wherein the gelatin layer encapsulates about 25 mg±about 5 or 10% of a PUFA composition, wherein the PUFA composition is the composition used in Epanova® or a generic form thereof.

In particular embodiments, the millicapsule is a spherical or approximately spherical soft porcine gelatin capsule with an overall diameter of about 4 mm±about 0.1, 0.2, 0.3, or 0.5 mm; wherein the gelatin forms a layer with a thickness of 0.10 to 0.25 mm, such as 0.15 mm to 0.24 mm, such as 0.18 to 0.24 mm; wherein the millicapsule further comprises a coating comprising a poly(ethylacrylate-methylmethacrylate) copolymer, such as poly(ethylacrylate-methylmethacrylate) 2:1 (for example NM30D), said coating having a thickness of 0.03 to 0.05 mm, such as 0.032 to 0.048 mm, such as 0.032 to 0.046 mm, such as 0.034 to 0.042 mm; and wherein the gelatin layer encapsulates about 25 mg±about 5 or 10% of a PUFA composition comprising EPA, substantially in free acid form, in an amount of 50 wt % to 60 wt %, DHA, substantially in free acid form, in an amount of 15 wt % to 25 wt % and DPA, substantially in free acid form, in an amount of 1 wt % to 8 wt %.

In particular embodiments, the millicapsule is a spherical or approximately spherical soft porcine gelatin capsule with an overall diameter of about 4 mm±about 0.1, 0.2, 0.3, or 0.5 mm; wherein the gelatin forms a layer with a thickness of 0.10 to 0.25 mm, such as 0.15 mm to 0.24 mm, such as 0.18 to 0.24 mm; wherein the millicapsule further comprises a coating comprising a poly(ethylacrylate-methylmethacrylate) copolymer, such as poly(ethylacrylate-methylmethacrylate) 2:1 (for example NM30D), said coating having a thickness of 0.03 to 0.05 mm, such as 0.032 to 0.048 mm, such as 0.032 to 0.046 mm, such as 0.034 to 0.042 mm; and wherein the gelatin layer encapsulates about 25 mg±about 5 or 10% of a PUFA composition comprising EPA, substantially in free acid form, in an amount of 50 wt % to 60 wt %, DHA, substantially in free acid form, in an amount of 17 wt % to 23 wt % and DPA, substantially in free acid form, in an amount of 1 wt % to 8 wt %.

In particular embodiments, the millicapsule is a spherical or approximately spherical soft porcine gelatin capsule with an overall diameter of about 4 mm±about 0.1, 0.2, 0.3, or 0.5 mm; wherein the gelatin forms a layer with a thickness of 0.10 to 0.25 mm, such as 0.15 mm to 0.24 mm, such as 0.18 to 0.24 mm; wherein the millicapsule further comprises a coating comprising a poly(ethylacrylate-methylmethacrylate) copolymer, such as poly(ethylacrylate-methylmethacrylate) 2:1 (for example NM30D), said coating having a thickness of 0.03 to 0.05 mm, such as 0.032 to 0.048 mm, such as 0.032 to 0.046 mm, such as 0.034 to 0.042 mm; and wherein the gelatin layer encapsulates about 25 mg±about 5 or 10% of a PUFA composition, wherein the PUFA composition is the composition used in Epanova® or a generic form thereof.

In particular embodiments, the millicapsule is a seamless soft gelatin capsule in which the gelatin consists essentially of porcine Type A gelatin of 200 bloom±about 5 or 10%, wherein the millicapsule is spherical or approximately spherical in shape with a diameter of about 4 mm±about 0.1, 0.2, 0.3, or 0.5 mm; wherein the gelatin layer encapsulates about 25 mg±about 5 or 10% of a PUFA composition comprising EPA, substantially in free acid form, in an amount of 50 wt % to 60 wt %, DHA, substantially in free acid form, in an amount of 15 wt % to 25 wt % and DPA, substantially in free acid form, in an amount of 1 wt % to 8 wt %.

In particular embodiments, the millicapsule is a seamless soft gelatin capsule in which the gelatin consists essentially of porcine Type A gelatin of 200 bloom±about 5 or 10%, wherein the millicapsule is spherical or approximately spherical in shape with a diameter of about 4 mm±about 0.1, 0.2, 0.3, or 0.5 mm; wherein the gelatin layer encapsulates about 25 mg±about 5 or 10% of a PUFA composition comprising EPA, substantially in free acid form, in an amount of 50 wt % to 60 wt %, DHA, substantially in free acid form, in an amount of 17 wt % to 23 wt % and DPA, substantially in free acid form, in an amount of 1 wt % to 8 wt %.

In particular embodiments, the millicapsule is a seamless soft gelatin capsule in which the gelatin consists essentially of porcine Type A gelatin of 200 bloom±about 5 or 10%, wherein the millicapsule is spherical or approximately spherical in shape with a diameter of about 4 mm±about 0.1, 0.2, 0.3, or 0.5 mm; wherein the millicapsule includes about 25 mg±about 5 or 10% of a PUFA composition as a liquid fill within the millicapsule, wherein the PUFA composition is the composition which is used in Epanova® or a generic form thereof.

In particular embodiments, the millicapsule is a seamless soft gelatin capsule in which the gelatin consists essentially of porcine Type A gelatin of 200 bloom±about 5 or 10%, wherein the millicapsule is spherical or approximately spherical in shape with a diameter of about 4 mm±about 0.1, 0.2, 0.3, or 0.5 mm; wherein the millicapsule comprises about 5% by weight of a coating comprising a poly(ethylacrylate-methylmethacrylate) 2:1 copolymer (such as Eudragit NM30D); and wherein the millicapsule includes about 25 mg±about 5 or 10% of a PUFA composition as a liquid fill within the millicapsule, wherein the PUFA composition comprises EPA, substantially in free acid form, in an amount of 50 wt % to 60 wt %, DHA, substantially in free acid form, in an amount of 15 wt % to 25 wt % and DPA, substantially in free acid form, in an amount of 1 wt % to 8 wt %.

In particular embodiments, the millicapsule is a seamless soft gelatin capsule in which the gelatin consists essentially of porcine Type A gelatin of 200 bloom±about 5 or 10%, wherein the millicapsule is spherical or approximately spherical in shape with a diameter of about 4 mm±about 0.1, 0.2, 0.3, or 0.5 mm; wherein the millicapsule comprises about 5% by weight of a coating comprising a poly(ethylacrylate-methylmethacrylate) 2:1 copolymer (such as Eudragit NM30D); and wherein the millicapsule includes about 25 mg±about 5 or 10% of a PUFA composition as a liquid fill within the millicapsule, wherein the PUFA composition comprises EPA, substantially in free acid form, in an amount of 50 wt % to 60 wt %, DHA, substantially in free acid form, in an amount of 17 wt % to 23 wt % and DPA, substantially in free acid form, in an amount of 1 wt % to 8 wt %.

In particular embodiments, the millicapsule is a seamless soft gelatin capsule in which the gelatin consists essentially of porcine Type A gelatin of 200 bloom±about 5 or 10%, wherein the millicapsule is spherical or approximately spherical in shape with a diameter of about 4 mm±about 0.1, 0.2, 0.3, or 0.5 mm; wherein the millicapsule comprises about 5% by weight of a coating comprising a poly(ethylacrylate-methylmethacrylate) 2:1 copolymer (such as Eudragit NM30D); and wherein the millicapsule includes about 25 mg±about 5 or 10% of a PUFA composition as a liquid fill within the millicapsule, wherein the PUFA composition is the composition which is used in Epanova® or a generic form thereof.

In particular embodiments, the millicapsule is a seamless soft gelatin capsule in which the gelatin comprises porcine Type A gelatin of 200 bloom±about 5 or 10%, wherein the millicapsule is spherical or approximately spherical in shape with a diameter of about 4 mm±about 0.1, 0.2, 0.3, or 0.5 mm; wherein the millicapsule includes about 25 mg±about 5 or 10% of a PUFA composition as a liquid fill within the millicapsule, wherein the PUFA composition comprises EPA, substantially in free acid form, in an amount of 50 wt % to 60 wt %, DHA, substantially in free acid form, in an amount of 15 wt % to 25 wt % and DPA, substantially in free acid form, in an amount of 1 wt % to 8 wt %.

In particular embodiments, the millicapsule is a seamless soft gelatin capsule in which the gelatin comprises porcine Type A gelatin of 200 bloom±about 5 or 10%, wherein the millicapsule is spherical or approximately spherical in shape with a diameter of about 4 mm±about 0.1, 0.2, 0.3, or 0.5 mm; wherein the millicapsule includes about 25 mg±about 5 or 10% of a PUFA composition as a liquid fill within the millicapsule, wherein the PUFA composition comprises EPA, substantially in free acid form, in an amount of 50 wt % to 60 wt %, DHA, substantially in free acid form, in an amount of 17 wt % to 23 wt % and DPA, substantially in free acid form, in an amount of 1 wt % to 8 wt %.

In particular embodiments, the millicapsule is a seamless soft gelatin capsule in which the gelatin comprises porcine Type A gelatin of 200 bloom±about 5 or 10%, wherein the millicapsule is spherical or approximately spherical in shape with a diameter of about 4 mm±about 0.1, 0.2, 0.3, or 0.5 mm; wherein the millicapsule includes about 25 mg±about 5 or 10% of a PUFA composition as a liquid fill within the millicapsule, wherein the PUFA composition is the composition which is used in Epanova® or a generic form thereof.

In particular embodiments, the millicapsule is a seamless soft gelatin capsule in which the gelatin comprises porcine Type A gelatin of 200 bloom±about 5 or 10%, wherein the millicapsule is spherical or approximately spherical in shape with a diameter of about 4 mm±about 0.1, 0.2, 0.3, or 0.5 mm; wherein the millicapsule comprises about 5% by weight of a coating comprising a poly(ethylacrylate-methylmethacrylate) 2:1 copolymer (such as Eudragit NM30D); and wherein the millicapsule includes about 25 mg±about 5 or 10% of a PUFA composition as a liquid fill within the millicapsule, wherein the PUFA composition comprises EPA, substantially in free acid form, in an amount of 50 wt % to 60 wt %, DHA, substantially in free acid form, in an amount of 15 wt % to 25 wt % and DPA, substantially in free acid form, in an amount of 1 wt % to 8 wt %.

In particular embodiments, the millicapsule is a seamless soft gelatin capsule in which the gelatin comprises porcine Type A gelatin of 200 bloom±about 5 or 10%, wherein the millicapsule is spherical or approximately spherical in shape with a diameter of about 4 mm±about 0.1, 0.2, 0.3, or 0.5 mm; wherein the millicapsule comprises about 5% by weight of a coating comprising a poly(ethylacrylate-methylmethacrylate) 2:1 copolymer (such as Eudragit NM30D); and wherein the millicapsule includes about 25 mg±about 5 or 10% of a PUFA composition as a liquid fill within the millicapsule, wherein the PUFA composition comprises EPA, substantially in free acid form, in an amount of 50 wt % to 60 wt %, DHA, substantially in free acid form, in an amount of 17 wt % to 23 wt % and DPA, substantially in free acid form, in an amount of 1 wt % to 8 wt %.

In particular embodiments, the millicapsule is a seamless soft gelatin capsule in which the gelatin comprises porcine Type A gelatin of 200 bloom±about 5 or 10%, wherein the millicapsule is spherical or approximately spherical in shape with a diameter of about 4 mm±about 0.1, 0.2, 0.3, or 0.5 mm; wherein the millicapsule comprises about 5% by weight of a coating comprising a poly(ethylacrylate-methylmethacrylate) 2:1 copolymer (such as Eudragit NM30D); and wherein the millicapsule includes about 25 mg±about 5 or 10% of a PUFA composition as a liquid fill within the millicapsule, wherein the PUFA composition is the composition which is used in Epanova® or a generic form thereof.

In the particular embodiments described above, it will be understood that the coating, where present is on the outside surface of the millicapsule and is applied on to the gelatin layer.

Millicapsule Stability

It will be understood that an essential requirement of a pharmaceutical product is that it remains suitable for use throughout its designated shelf life, in other words that it remains stable. The stability of a proposed product is tested during its development to understand how long it will remain suitable for use after manufacture. A long shelf life is preferable.

As demonstrated in the Examples herein, the millicapsules described herein are manufactured using gelatin which also contains glycerol and some sorbitol as plasticizers. Epanova® 1 g capsules also contain glycerol and sorbitol as plasticizers.

The skilled person will understand that it is possible, over time, for the free fatty acids in the PUFA composition described herein to interact somewhat with the glycerol in the gelatin to form glycerides (including di- and tri-glyceride) derivatives of the free fatty acids. For Epanova 1 g capsules, such glyceride formation is a factor in limiting the shelf life of the commercial product to 30 months.

It is possible for the small, seamless millicapsules described herein to be manufactured to contain less plasticizer than is required for manufacture of the large soft gelatin capsules (approximately a quarter of the amount of glycerol per gram of gelatin may be used in the millicapsules compared to the 1 g capsules). This reduction in glycerol content would be expected to result in somewhat lower glyceride formation on storage.

However, the surface area to volume ratio of the millicapsules is much higher for the millicapsules than the 1 g Epanova® capsules. This would be expected to increase formation of glycerides in the millicapsules because there is a proportionally greater interaction between the oil and the millicapsule interior surface.

Surprisingly, we have found that the millicapsules, whether coated or uncoated, show significantly less glyceride formation on long term storage than the 1 g Epanova® capsules, which should result in a significantly longer shelf life in this respect (although there may differences in other parameters which may also impact, positively or negatively, on the shelf life). Stability studies showing the comparison between the millicapsules and 1 g Epanova® capsules on glyceride formation are described in the Examples hereinafter.

In other embodiments, unit dosage forms comprising a plurality of millicapsules exhibit greater stability and have a longer shelf life than the single capsule reference unit dosage form, such as that approved by the US FDA for Epanova®.

In other embodiments, unit dosage forms comprising a plurality of millicapsules exhibit greater stability in respect of glyceride formation than the single capsule reference unit dosage form, such as that approved by the US FDA for Epanova®.

In particular embodiments, there is provided a spherical or approximately spherical soft porcine gelatin millicapsule with an overall diameter of about 4 mm±about 0.1, 0.2, 0.3, or 0.5 mm; wherein the gelatin forms a layer with a thickness of 0.10 to 0.25 mm, such as 0.15 mm to 0.24 mm, such as 0.18 to 0.24 mm; wherein the gelatin layer encapsulates about 25 mg±about 5 or 10% of a PUFA composition comprising EPA, substantially in free acid form, in an amount of 50 wt % to 60 wt %, DHA, substantially in free acid form, in an amount of 15 wt % to 25 wt % and DPA, substantially in free acid form, in an amount of 1 wt % to 8 wt %; and wherein less than about 2% a/a, such as <1.8% a/a, such as <1.5% a/a of glycerides are formed after the millicapsule has been stored at 25° C./60% relative humidity for 12 months.

For the avoidance of doubt, % a/a is area percent on a GC chromatogram of the composition.

In particular embodiments, there is provided a spherical or approximately spherical soft porcine gelatin millicapsule with an overall diameter of about 4 mm±about 0.1, 0.2, 0.3, or 0.5 mm; wherein the gelatin forms a layer with a thickness of 0.10 to 0.25 mm, such as 0.15 mm to 0.24 mm, such as 0.18 to 0.24 mm; wherein the gelatin layer encapsulates about 25 mg±about 5 or 10% of a PUFA composition comprising EPA, substantially in free acid form, in an amount of 50 wt % to 60 wt %, DHA, substantially in free acid form, in an amount of 17 wt % to 23 wt % and DPA, substantially in free acid form, in an amount of 1 wt % to 8 wt %; and wherein less than about 2% a/a, such as <1.8% a/a, such as <1.5% a/a of glycerides are formed after the millicapsule has been stored at 25° C./60% relative humidity for 12 months.

In particular embodiments, there is provided a spherical or approximately spherical soft porcine gelatin millicapsule with an overall diameter of about 4 mm±about 0.1, 0.2, 0.3, or 0.5 mm; wherein the gelatin forms a layer with a thickness of 0.10 to 0.25 mm, such as 0.15 mm to 0.24 mm, such as 0.18 to 0.24 mm; wherein the gelatin layer encapsulates about 25 mg±about 5 or 10% of a PUFA composition, wherein the PUFA composition is the composition which is used in Epanova® or a generic form thereof; and wherein less than about 2% a/a, such as <1.8% a/a, such as <1.5% a/a of glycerides are formed after the millicapsule has been stored at 25° C./60% relative humidity for 12 months.

In particular embodiments, there is provide a spherical or approximately spherical soft porcine gelatin millicapsule with an overall diameter of about 4 mm±about 0.1, 0.2, 0.3, or 0.5 mm; wherein the gelatin forms a layer with a thickness of 0.10 to 0.25 mm, such as 0.15 mm to 0.24 mm, such as 0.18 to 0.24 mm; wherein the millicapsule further comprises a coating comprising a poly(ethylacrylate-methylmethacrylate) copolymer, such as poly(ethylacrylate-methylmethacrylate 2:1 (for example NM30D), said coating having a thickness of 0.03 to 0.05 mm, such as 0.032 to 0.048 mm, such as 0.032 to 0.046 mm, such as 0.034 to 0.042 mm; wherein the gelatin layer encapsulates about 25 mg±about 5 or 10% of a PUFA composition comprising EPA, substantially in free acid form, in an amount of 50 wt % to 60 wt %, DHA, substantially in free acid form, in an amount of 15 wt % to 25 wt % and DPA, substantially in free acid form, in an amount of 1 wt % to 8 wt %; and wherein less than about 2% a/a, such as <1.8% a/a, such as <1.5% a/a of glycerides are formed after the millicapsule has been stored at 25° C./60% relative humidity for 12 months.

In particular embodiments, there is provided a spherical or approximately spherical soft porcine gelatin millicapsule with an overall diameter of about 4 mm±about 0.1, 0.2, 0.3, or 0.5 mm; wherein the gelatin forms a layer with a thickness of 0.10 to 0.25 mm, such as 0.15 mm to 0.24 mm, such as 0.18 to 0.24 mm; wherein the millicapsule further comprises a coating comprising a poly(ethylacrylate-methylmethacrylate) copolymer, such as poly(ethylacrylate-methylmethacrylate 2:1 (for example NM30D), said coating having a thickness of 0.03 to 0.05 mm, such as 0.032 to 0.048 mm, such as 0.032 to 0.046 mm, such as 0.034 to 0.042 mm; and wherein the gelatin layer encapsulates about 25 mg±about 5 or 10% of a PUFA composition comprising EPA, substantially in free acid form, in an amount of 50 wt % to 60 wt %, DHA, substantially in free acid form, in an amount of 17 wt % to 23 wt % and DPA, substantially in free acid form, in an amount of 1 wt % to 8 wt %; and wherein less than about 2% a/a, such as <1.8% a/a, such as <1.5% a/a of glycerides are formed after the millicapsule has been stored at 25° C./60% relative humidity for 12 months.

In particular embodiments, there is provided a spherical or approximately spherical soft porcine gelatin millicapsule with an overall diameter of about 4 mm±about 0.1, 0.2, 0.3, or 0.5 mm; wherein the gelatin forms a layer with a thickness of 0.10 to 0.25 mm, such as 0.15 mm to 0.24 mm, such as 0.18 to 0.24 mm; wherein the millicapsule further comprises a coating comprising a poly(ethylacrylate-methylmethacrylate) copolymer, such as poly(ethylacrylate-methylmethacrylate 2:1 (for example NM30D), said coating having a thickness of 0.03 to 0.05 mm, such as 0.032 to 0.048 mm, such as 0.032 to 0.046 mm, such as 0.034 to 0.042 mm; wherein the gelatin layer encapsulates about 25 mg±about 5 or 10% of a PUFA composition, wherein the PUFA composition is the composition which is used in Epanova® or a generic form thereof; and wherein less than about 2% a/a, such as <1.8% a/a, such as <1.5% a/a of glycerides are formed after the millicapsule has been stored at 25° C./60% relative humidity for 12 months.

In particular embodiments, there is provided a seamless soft gelatin millicapsule in which the gelatin consists essentially of porcine Type A gelatin of 200 bloom±about 5 or 10%, wherein the millicapsule is spherical or approximately spherical in shape with a diameter of about 4 mm±about 0.1, 0.2, 0.3, or 0.5 mm; wherein the millicapsule includes about 25 mg±about 5 or 10% of a PUFA composition as a liquid fill within the millicapsule, wherein the PUFA composition comprises EPA, substantially in free acid form, in an amount of 50 wt % to 60 wt %, DHA, substantially in free acid form, in an amount of 15 wt % to 25 wt % and DPA, substantially in free acid form, in an amount of 1 wt % to 8 wt %; and wherein less than about 2% a/a, such as <1.8% a/a, such as <1.5% a/a of glycerides are formed after the millicapsule has been stored at 25° C./60% relative humidity for 12 months.

In particular embodiments, there is provided a seamless soft gelatin millicapsule in which the gelatin consists essentially of porcine Type A gelatin of 200 bloom±about 5 or 10%, wherein the millicapsule is spherical or approximately spherical in shape with a diameter of about 4 mm±about 0.1, 0.2, 0.3, or 0.5 mm; wherein the millicapsule includes about 25 mg±about 5 or 10% of a PUFA composition as a liquid fill within the millicapsule, wherein the PUFA composition comprises EPA, substantially in free acid form, in an amount of 50 wt % to 60 wt %, DHA, substantially in free acid form, in an amount of 17 wt % to 23 wt % and DPA, substantially in free acid form, in an amount of 1 wt % to 8 wt %; and wherein less than about 2% a/a, such as <1.8% a/a, such as <1.5% a/a of glycerides are formed after the millicapsule has been stored at 25° C./60% relative humidity for 12 months.

In particular embodiments, there is provided a seamless soft gelatin millicapsule in which the gelatin consists essentially of porcine Type A gelatin of 200 bloom±about 5 or 10%, wherein the millicapsule is spherical or approximately spherical in shape with a diameter of about 4 mm±about 0.1, 0.2, 0.3, or 0.5 mm; wherein the millicapsule includes about 25 mg±about 5 or 10% of a PUFA composition as a liquid fill within the millicapsule, wherein the PUFA composition is the composition which is used in Epanova® or a generic form thereof; and wherein less than about 2% a/a, such as <1.8% a/a, such as <1.5% a/a of glycerides are formed after the millicapsule has been stored at 25° C./60% relative humidity for 12 months.

In particular embodiments, there is provided a seamless soft gelatin millicapsule in which the gelatin consists essentially of porcine Type A gelatin of 200 bloom±about 5 or 10%, wherein the millicapsule is spherical or approximately spherical in shape with a diameter of about 4 mm±about 0.1, 0.2, 0.3, or 0.5 mm; wherein the millicapsule comprises about 5% by weight of a coating comprising a poly(ethylacrylate-methylmethacrylate) 2:1 copolymer (such as Eudragit® NM30D); wherein the millicapsule includes about 25 mg±about 5 or 10% of a PUFA composition as a liquid fill within the millicapsule, wherein the PUFA composition comprises EPA, substantially in free acid form, in an amount of 50 wt % to 60 wt %, DHA, substantially in free acid form, in an amount of 15 wt % to 25 wt % and DPA, substantially in free acid form, in an amount of 1 wt % to 8 wt %; and wherein less than about 2% a/a, such as <1.8% a/a, such as <1.5% a/a of glycerides are formed after the millicapsule has been stored at 25° C./60% relative humidity for 12 months.

In particular embodiments, there is provided a seamless soft gelatin millicapsule in which the gelatin consists essentially of porcine Type A gelatin of 200 bloom±about 5 or 10%, wherein the millicapsule is spherical or approximately spherical in shape with a diameter of about 4 mm±about 0.1, 0.2, 0.3, or 0.5 mm; wherein the millicapsule comprises about 5% by weight of a coating comprising a poly(ethylacrylate-methylmethacrylate) 2:1 copolymer (such as Eudragit® NM30D); wherein the millicapsule includes about 25 mg±about 5 or 10% of a PUFA composition as a liquid fill within the millicapsule, wherein the PUFA composition comprises EPA, substantially in free acid form, in an amount of 50 wt % to 60 wt %, DHA, substantially in free acid form, in an amount of 17 wt % to 23 wt % and DPA, substantially in free acid form, in an amount of 1 wt % to 8 wt %; and wherein less than about % a/a, such as <1.8% a/a, such as <1.5% a/a of glycerides are formed after the millicapsule has been stored at 25° C./60% relative humidity for 12 months.

In particular embodiments, there is provided a seamless soft gelatin millicapsule in which the gelatin consists essentially of porcine Type A gelatin of 200 bloom±about 5 or 10%, wherein the millicapsule is spherical or approximately spherical in shape with a diameter of about 4 mm±about 0.1, 0.2, 0.3, or 0.5 mm; wherein the millicapsule comprises about 5% by weight of a coating comprising a poly(ethylacrylate-methylmethacrylate) 2:1 copolymer (such as Eudragit® NM30D); wherein the millicapsule includes about 25 mg±about 5 or 10% of a PUFA composition as a liquid fill within the millicapsule, wherein the PUFA composition is the composition which is used in Epanova® or a generic form thereof; and wherein less than about 2% a/a, such as <1.8% a/a, such as <1.5% a/a of glycerides are formed after the millicapsule has been stored at 25° C./60% relative humidity for 12 months.

In particular embodiments, there is provided a seamless soft gelatin millicapsule in which the gelatin comprises porcine Type A gelatin of 200 bloom±about 5 or 10%, wherein the millicapsule is spherical or approximately spherical in shape with a diameter of about 4 mm±about 0.1, 0.2, 0.3, or 0.5 mm; wherein the millicapsule includes about 25 mg±about 5 or 10% of a PUFA composition as a liquid fill within the millicapsule, wherein the PUFA composition comprises EPA, substantially in free acid form, in an amount of 50 wt % to 60 wt %, DHA, substantially in free acid form, in an amount of 15 wt % to 25 wt % and DPA, substantially in free acid form, in an amount of 1 wt % to 8 wt %; and wherein less than about 2% a/a, such as <1.8% a/a, such as <1.5% a/a of glycerides are formed after the millicapsule has been stored at 25° C./60% relative humidity for 12 months.

In particular embodiments, there is provided a seamless soft gelatin millicapsule in which the gelatin comprises porcine Type A gelatin of 200 bloom±about 5 or 10%, wherein the millicapsule is spherical or approximately spherical in shape with a diameter of about 4 mm±about 0.1, 0.2, 0.3, or 0.5 mm; wherein the millicapsule includes about 25 mg±about 5 or 10% of a PUFA composition as a liquid fill within the millicapsule, wherein the PUFA composition comprises EPA, substantially in free acid form, in an amount of 50 wt % to 60 wt %, DHA, substantially in free acid form, in an amount of 17 wt % to 23 wt % and DPA, substantially in free acid form, in an amount of 1 wt % to 8 wt %; and wherein less than about 2% a/a, such as <1.8% a/a, such as <1.5% a/a of glycerides are formed after the millicapsule has been stored at 25° C./60% relative humidity for 12 months.

In particular embodiments, there is provided a seamless soft gelatin millicapsule in which the gelatin comprises porcine Type A gelatin of 200 bloom±about 5 or 10%, wherein the millicapsule is spherical or approximately spherical in shape with a diameter of about 4 mm±about 0.1, 0.2, 0.3, or 0.5 mm; wherein the millicapsule includes about 25 mg±about 5 or 10% of a PUFA composition as a liquid fill within the millicapsule, wherein the PUFA composition is the composition which is that used in Epanova® or a generic form thereof; and wherein less than about 2% a/a, such as <1.8% a/a, such as <1.5% a/a of glycerides are formed after the millicapsule has been stored at 25° C./60% relative humidity for 12 months.

In particular embodiments, there is provided a seamless soft gelatin millicapsule in which the gelatin comprises porcine Type A gelatin of 200 bloom±about 5 or 10%, wherein the millicapsule is spherical or approximately spherical in shape with a diameter of about 4 mm±about 0.1, 0.2, 0.3, or 0.5 mm; wherein the millicapsule comprises about 5% by weight of a coating comprising a poly(ethylacrylate-methylmethacrylate) 2:1 copolymer (such as Eudragit® NM30D); and wherein the millicapsule includes about 25 mg±about 5 or 10% of a PUFA composition as a liquid fill within the millicapsule, wherein the PUFA composition comprises EPA, substantially in free acid form, in an amount of 50 wt % to 60 wt %, DHA, substantially in free acid form, in an amount of 15 wt % to 25 wt % and DPA, substantially in free acid form, in an amount of 1 wt % to 8 wt %; and wherein less than about 2% a/a, such as <1.8% a/a, such as <1.5% a/a of glycerides are formed after the millicapsule has been stored at 25° C./60% relative humidity for 12 months.

In particular embodiments, there is provided a seamless soft gelatin millicapsule in which the gelatin comprises porcine Type A gelatin of 200 bloom±about 5 or 10%, wherein the millicapsule is spherical or approximately spherical in shape with a diameter of about 4 mm±about 0.1, 0.2, 0.3, or 0.5 mm; wherein the millicapsule comprises about 5% by weight of a coating comprising a poly(ethylacrylate-methylmethacrylate) 2:1 copolymer (such as Eudragit® NM30D); and wherein the millicapsule includes about 25 mg±about 5 or 10% of a PUFA composition as a liquid fill within the millicapsule, wherein the PUFA composition comprises EPA, substantially in free acid form, in an amount of 50 wt % to 60 wt %, DHA, substantially in free acid form, in an amount of 17 wt % to 23 wt % and DPA, substantially in free acid form, in an amount of 1 wt % to 8 wt %; and wherein less than about 2% a/a, such as <1.8% a/a, such as <1.5% a/a of glycerides are formed after the millicapsule has been stored at 25° C./60% relative humidity for 12 months.

In particular embodiments, there is provided a seamless soft gelatin millicapsule in which the gelatin comprises porcine Type A gelatin of 200 bloom±about 5 or 10%, wherein the millicapsule is spherical or approximately spherical in shape with a diameter of about 4 mm±about 0.1, 0.2, 0.3, or 0.5 mm; wherein the millicapsule comprises about 5% by weight of a coating comprising a poly(ethylacrylate-methylmethacrylate) 2:1 copolymer (such as Eudragit® NM30D); and wherein the millicapsule includes about 25 mg±about 5 or 10% of a PUFA composition as a liquid fill within the millicapsule, wherein the PUFA composition is the composition which is used in Epanova® or a generic form thereof; and wherein less than about 2% a/a, such as <1.8% a/a, such as <1.5% a/a of glycerides are formed after the millicapsule has been stored at 25° C./60% relative humidity for 12 months.

Methods of Treatment

In another aspect, methods of treatment are provided that employ the capsular dosage forms provide herein.

Treatment of Severe Hypertriglyceridemia (>500 mg/dL)

In a first series of treatment embodiments, methods of treating severe hypertriglyceridemia are provided.

The methods comprise orally administering the capsular dosage forms described above (e.g., millicapsules and unit dosage forms comprising a plurality of millicapsules containing the PUFA composition therein) to a patient having pre-treatment serum or plasma triglyceride levels ≥500 mg/dL, in an amount and for a duration sufficient to reduce serum or plasma triglyceride levels below pre-treatment levels. In typical embodiments, each unit dose is administered as one or as a plurality of the unit dosage forms described above.

In some embodiments, the capsular dosage form is administered in an amount and for a duration sufficient to reduce plasma levels of triglycerides in a subject in need thereof. Pre-treatment plasma levels of triglycerides may be obtained as described in U.S. Patent Publication No. 2013/0177643 (and references disclosed therein for exemplary methods for measuring triglycerides), which is incorporated herein in its entirety. In various embodiments, the capsular dosage form is administered in an amount and for a duration effective to reduce serum or plasma triglyceride levels by at least about 5%, 6%, 7%, 8%, or at least about 9% below pre-treatment levels. In certain embodiments, the capsular dosage form is administered in an amount and for a duration effective to reduce serum or plasma triglyceride levels by at least 10%, 11%, 12%, 13%, 14%, 15%, 16%, 17%, 18% or 19% below pre-treatment levels. In particular embodiments, the capsular dosage form is administered in an amount and for a duration effective to reduce serum or plasma triglyceride levels by at least about 20% below pre-treatment levels. In various embodiments, the capsular dosage form is administered in an amount and for a duration effective to reduce serum or plasma triglycerides by at least about 25%, 30%, 35%, 40%, 45%, even at least about 50% below pre-treatment levels.

In certain embodiments, the plasma level of triglycerides is reduced by about 50 mg/dL or more relative to a pre-treatment plasma level of triglycerides, such as by about 60 mg/dL or more, such as by about 70 mg/dL or more, such as by about 80 mg/dL or more, such as by about 90 mg/dL or more, such as by about 100 mg/dL or more, such as by about 110 mg/dL or more, such as by about 120 mg/dL or more, such as by about 130 mg/dL or more, such as by about 140 mg/dL or more, such as by about 150 mg/dL or more, such as by about 160 mg/dL or more, such as by about 170 mg/dL or more, such as by about 180 mg/dL or more, such as by about 190 mg/dL or more, such as by about 200 mg/dL or more, such as by about 250 mg/dL or more relative to a pre-treatment plasma level of triglycerides. The methods of the present disclosure may reduce the plasma level of triglycerides by about 500 mg/dL or less, such as about 400 mg/dL or less, such as about 300 mg/dL or less relative to a pre-treatment plasma level of triglycerides.

In some embodiments, the plasma level of triglycerides is reduced to about 700 mg/dL or less, such as about 650 mg/dL or less, such as about 600 mg/dL or less, such as about 550 mg/dL or less, such as about 500 mg/dL or less, such as about 450 mg/dL or less, such as about 400 mg/dL or less, such as about 350 mg/dL or less, such as about 300 mg/dL or less, such as about 250 mg/dL or less, such as about 200 mg/dL or less. In a series of embodiments, the capsular dosage form is administered in an amount and for a duration effective to reduce serum or plasma triglyceride levels by at least about 50 mg/dL, 60 mg/dL, 70 mg/dL, 80 mg/dL, 90 mg/dL, even at least about 100 mg/dL. In certain embodiments, the capsular dosage form is administered in an amount and for a duration effective to reduce serum or plasma triglyceride levels by at least about 110 mg/dL, 120 mg/dL, 130 mg/dL, 140 mg/dL, even at least about 150 mg/dL. In specific embodiments, the capsular dosage form is administered in an amount and for a duration effective to reduce serum or plasma triglyceride levels by at least about 160 mg/dL, 170 mg/dL, 180 mg/dL, even at least about 190 mg/dL or 200 mg/dL.

In some embodiments, the capsular dosage form is administered in an amount and for a duration effective to decrease non-HDL-c levels by at least about 1%, 2%, 3%, 4%, 5%, 6%, 7%, 8%, 9%, even at least about 10% below pre-treatment levels.

In various embodiments, the capsular dosage form is administered in an amount and for a duration effective to increase HDL-c levels by at least about 1% above pre-treatment levels. In certain embodiments, the capsular dosage form is administered in an amount and for a duration sufficient to increase HDL-c by at least about 2%, 3%, 4%, even at least about 5%, 6%, 7%, 8%, 9%, or 10% above pre-treatment levels.

In certain embodiments, the capsular dosage form is administered in an amount and for a duration effective to reduce the total cholesterol:HDL-c ("TC/HDL") ratio by at least about 1% below pre-treatment levels. In some embodiments, the capsular dosage form is administered in an amount and for a duration sufficient to reduce the TC/HDL ratio by at least about 2%, 3%, 4%, 5%, 6%, 7%, 8%, even at least about 9% or at least about 10% below pre-treatment levels.

In some embodiments, the capsular dosage form is administered in an amount and for a duration effective to decrease VLDL-c levels by at least about 5%, 6%, 7%, 8%, 9%, or at least about 10% below pre-treatment levels. In certain embodiments, the capsular dosage form is administered in an amount and for a duration sufficient to decrease VLDL-c levels by at least about 11%, 12%, 13%, 14%, 15%, 16%, 17%, even at least about 18%, 19%, or 20% below pre-treatment levels. In particular embodiments, the capsular dosage form is administered in an amount and for a duration sufficient to decrease VLDL-c levels by at least about 21%, 22%, 23%, 24%, even at least about 25% below pre-treatment levels.

In a variety of embodiments, the capsular dosage form is administered in an amount and for a duration effective to decrease ApoCIII levels. In certain embodiments, the capsular dosage form is administered in an amount and for a duration sufficient to decrease ApoCIII levels by at least about 1%, 2%, 3%, 4%, 5%, 6%, 7%, even at least about 8%, 9% or 10% below pre-treatment levels.

In some embodiments, the capsular dosage form is administered in an amount and for a duration effective to increase plasma EPA levels by at least 100% above pre-treatment levels. In certain embodiments, the capsular dosage form is administered in an amount and for a duration effective to increase plasma EPA levels by at least about 200%, 250%, 300%, even at least about 350%, 400%, 450% or at least about 500% above pre-treatment levels. In selected embodiments, the capsular dosage form is administered for a time and in an amount effective to increase plasma EPA levels by at least about 550%, 600%, 650%, even at least about 700% above pre-treatment levels.

In various embodiments, the capsular dosage form is administered in an amount and for a duration effective to increase plasma DHA levels by at least about 50% above pre-treatment levels. In particular embodiments, the capsular dosage form is administered in an amount and for a duration effective to increase plasma DHA levels by at least about 55%, 60%, 65%, 70%, even at least about 75%, 80%, 85%, or 90% above pre-treatment levels.

In a series of embodiments, the capsular dosage form is administered in an amount and for a duration effective to increase plasma DPA levels by at least about 50% above pre-treatment levels. In some embodiments, the capsular dosage form is administered in an amount and for a duration effective to increase plasma DPA levels by at least about 55%, 60%, 65%, 70%, 75%, even at least about 80%, 85%, 90%, 95%, or 100% above pre-treatment levels. In selected embodiments, the capsular dosage form is administered in an amount and for a duration effective to increase plasma DPA levels by at least about 110%, 120%, even at least about 125% above pre-treatment levels.

In a series of embodiments, the capsular dosage form is administered in an amount and for a duration effective to reduce arachidonic acid (AA) concentration in plasma by at least about 5% below pre-treatment levels. In certain embodiments, the capsular dosage form is administered in an amount and for a duration effective to reduce arachidonic (AA) concentration in plasma by at least about 6%, 7%, 8%, 9%, 10%, even at least about 11%, 12%, 13%, 14%, even at least about 15%, 16%, 17%, 18%, 19%, 20%, or 21%, 22%, 23%, 24% even at least about 25% below pre-treatment levels.

In certain embodiments, the capsular dosage form is administered in an amount, and for a duration, effect to reduce plasma arachidonic acid concentration by at least about 25 µg/mL. In some embodiments, the capsular dosage form is administered in an amount and for a duration sufficient to reduce plasma AA levels by at least about 50 µg/mL, 55 µg/mL, 60 µg/mL, 65 µg/mL, even at least about 70 µg/mL, 75 µg/mL, 80 µg/mL, 85 µg/mL, 90 µg/mL, even at least about 95 µg/mL or 100 µg/mL.

In certain embodiments, the effective amount is at least about 2 g per day of the PUFA composition. In various embodiments, the effective amount is at least about 3 g per day of the PUFA composition. In particular embodiments, the effective amount is at least about 4 g per day of the PUFA composition. In typical embodiments, the effective amount is about 2 g per day of the PUFA composition. In certain embodiments, the effective amount is about 4 g per day of the PUFA composition.

In typical embodiments, the capsular dosage form is administered for at least 30 days. In certain embodiments, the capsular dosage form is administered for at least 60 days. In particular embodiments, the capsular dosage form is administered for at least 90 days, 120 days, 180 days, 240 days, or at least 360 days. In certain embodiments, the capsular dosage form is administered indefinitely.

In some embodiments, the capsular dosage form is administered daily. In other embodiments, the capsular dosage form is administered every other day.

In particular embodiments, the daily dosage of capsular dosage form is administered in a single daily dose. In other embodiments, the capsular dosage form is administered in divided doses, with the daily dose divided into two administrations, three administrations, or even four administrations, over the course of the day.

In certain embodiments, the capsular dosage form is administered with food. In certain embodiments, the capsular dosage form is administered with a low fat meal. In other embodiments, the capsular dosage form is administered without food. In certain embodiments, the capsular dosage form is administered in the fasting state.

The methods, in certain embodiments, further comprising co-administering a statin. In particular embodiments, the statin is selected from the group consisting of: pravastatin, lovastatin, simvastatin, atorvastatin, fluvastatin, rosuvastatin, tenivastatin, and pitavastatin.

The term "co-administration," as used herein, refers to the simultaneous, concurrent, or sequential administration of two therapeutic agents. "Simultaneous administration," as used herein, refers to administration of the PUFA composition and second therapeutic agent in a single unit dosage form. "Concurrent administration," as used herein, refers to the administration of the PUFA composition and second therapeutic agent in separate unit dosage forms within a short period of time of one another, such as within about 0.5, 1, 2, 5, 10, 15, 30, or 60 minutes, or essentially administering the two drugs at the same time but in different dosage forms. "Sequential administration," as used herein, refers to first administration of either the PUFA composition or second therapeutic agent after which administration of the other drug is commenced. The period of time between administration of the first drug and the second drug may be within hours, e.g., 1, 2, 3, 4, 6, or 12 hours, or the period of time between administrations may be extended, e.g., days, weeks, etc. In certain embodiments, two therapeutic agents may be administered by one or more methods of simultaneous, concurrent, and sequential administration.

Treatment of Hypertriglyceridemia (200-500 mg/dL)

In another series of treatment embodiments, methods of treating patients who have pre-treatment serum or plasma triglyceride levels of about 200 mg/dL to about 500 mg/dL are provided. In certain embodiments, the patients are already on statin therapy; in these patients, the pre-treatment serum or plasma triglyceride levels are those measured during statin treatment, prior to administration of the capsular dosage form described above.

The method comprises orally administering an effective amount of a statin, and further administering the capsular dosage form described herein, orally, in an amount and for a duration sufficient to lower serum or plasma triglyceride levels below levels measured prior to treatment with the capsular dosage form described herein. The capsular dosage form and the statin need not be administered at the same time, with the same dosage schedule, or even on the same days. It is sufficient that the two be administered in sufficient temporal proximity that the patient receives therapeutic benefit concurrently from both.

In certain embodiments, the capsular dosage form is administered in an amount and for a duration sufficient to reduce serum or plasma triglyceride levels by at least about 5% below pre-treatment levels. In various embodiments, the capsular dosage form is administered in an amount and for a duration sufficient to reduce serum or plasma triglyceride levels by at least about 6%, 7%, 8%, 9%, 10%, 11%, 12%, 13%, 14%, 15%, even at least about 16%, 17%, 18%, 19%, or at least about 20% below pre-treatment levels.

In some embodiments, the capsular dosage is administered in an amount and for a duration sufficient to reduce non-HDL-cholesterol by at least about 1%, at least about 2%, at least about 3%, 4%, 5%, even at least about 7%, 8%, 9%, or at least about 10% below pre-treatment levels.

In a series of embodiments, the capsular dosage form is administered in an amount and for a duration sufficient to raise HDL-c levels by at last about 1%, 2%, 3% or more above pre-treatment levels.

In some embodiments, the capsular dosage form is administered in an amount and for a duration effective to increase plasma EPA levels by at least 100% above pre-treatment levels. In certain embodiments, the capsular dosage form is administered in an amount and for a duration effective to increase plasma EPA levels by at least about 200%, 250%, 300%, even at least about 350%, 400%, 450% or at least about 500% above pre-treatment levels. In selected embodiments, the capsular dosage form is administered for a time and in an amount effective to increase plasma EPA levels by at least about 550%, 600%, 650%, even at least about 700% above pre-treatment levels.

In various embodiments, the capsular dosage form is administered in an amount and for a duration effective to increase plasma DHA levels by at least about 50% above pre-treatment levels. In particular embodiments, the capsular dosage form is administered in an amount and for a duration effective to increase plasma DHA levels by at least about 55%, 60%, 65%, 70%, even at least about 75%, 80%, 85%, or 90% above pre-treatment levels.

In a series of embodiments, the capsular dosage form is administered in an amount and for a duration effective to increase plasma DPA levels by at least about 50% above pre-treatment levels. In some embodiments, the capsular dosage form is administered in an amount and for a duration effective to increase plasma DPA levels by at least about 55%, 60%, 65%, 70%, 75%, even at least about 80%, 85%, 90%, 95%, or 100% above pre-treatment levels. In selected embodiments, the capsular dosage form is administered in an amount and for a duration effective to increase plasma DPA levels by at least about 110%, 120%, even at least about 125% above pre-treatment levels.

In a series of embodiments, the capsular dosage form is administered in an amount and for a duration effective to reduce arachidonic acid (AA) concentration in plasma by at least about 5% below pre-treatment levels. In certain embodiments, the capsular dosage form is administered in an amount and for a duration effective to reduce arachidonic (AA) concentration in plasma by at least about 6%, 7%, 8%, 9%, 10%, even at least about 11%, 12%, 13%, 14%, even at least about 15%, 16%, 17%, 18%, 19%, 20%, or 21%, 22%, 23%, 24% even at least about 25% below pre-treatment levels.

In certain embodiments, the capsular dosage form is administered in an amount, and for a duration, effect to reduce plasma arachidonic acid concentration by at least about 25 µg/mL. In some embodiments, the capsular dosage form is administered in an amount and for a duration sufficient to reduce plasma AA levels by at least about 50 µg/mL, 55 µg/mL, 60 µg/mL, 65 µg/mL, even at least about 70 µg/mL, 75 µg/mL, 80 µg/mL, 85 µg/mL, 90 µg/mL, even at least about 95 µg/mL or 100 µg/mL.

In various embodiments, the capsular dosage form described in herein is administered in unit dosage forms as described above.

In various embodiments, the capsular dosage form is administered to provide the PUFA composition in an amount of at least about 1 g per day. In some embodiments, the capsular dosage form is administered to provide the PUFA composition in an amount of at least about 2 g/day. In certain embodiments, the capsular dosage form is administered to provide the PUFA composition in an amount of at least about 3 g/day. In particular embodiments, the capsular dosage form is administered to provide the PUFA composition in an amount of at least about 4 g/day. In typical embodiments, the capsular dosage form is administered to provide the PUFA composition in an amount of about 2 g/day. In certain embodiments, the capsular dosage form is administered to provide the PUFA composition in an amount of about 3 g/day or about 4 g per day.

Treatment to Increase Plasma EPA:AA Ratios

Methods are also provided for increasing the EPA:AA ratio, without regard to the patient's pre-treatment plasma triglyceride levels. The methods comprise administering the capsular dosage form described herein to a patient having an EPA:AA ratio below about 0.25, in an amount and for duration sufficient to increase the patient's EPA:AA ratio to at least about 0.25. In some embodiments, the capsular dosage form is administered in an amount and for a duration sufficient to increase the patient's EPA:AA ratio to at least about 0.3, at least about 0.35, at least about 0.40, at least about 0.45, at least about 0.50, even to a level of at least about 0.55, 0.60, 0.61, 0.62, 0.63, 0.64, or 0.65.

In certain embodiments, the method comprises administering the capsular dosage form in an amount and for a duration effective to increase plasma EPA levels by at least 100% above pre-treatment levels. In certain embodiments, the capsular dosage form is administered in an amount and for a duration effective to increase plasma EPA levels by at least about 200%, 250%, 300%, even at least about 350%, 400%, 450% or at least about 500% above pre-treatment levels. In selected embodiments, the capsular dosage form is administered for a time and in an amount effective to increase plasma EPA levels by at least about 550%, 600%, 650%, even at least about 700% above pre-treatment levels.

In various embodiments, the capsular dosage form is administered in an amount and for a duration effective to increase plasma DHA levels by at least about 50% above pre-treatment levels. In particular embodiments, the capsular dosage form is administered in an amount and for a duration effective to increase plasma DHA levels by at least about 55%, 60%, 65%, 70%, even at least about 75%, 80%, 85%, or 90% above pre-treatment levels.

In a series of embodiments, the capsular dosage form is administered in an amount and for a duration effective to increase plasma DPA levels by at least about 50% above pre-treatment levels. In some embodiments, the capsular dosage form is administered in an amount and for a duration effective to increase plasma DPA levels by at least about 55%, 60%, 65%, 70%, 75%, even at least about 80%, 85%, 90%, 95%, or 100% above pre-treatment levels. In selected embodiments, the capsular dosage form is administered in an amount and for a duration effective to increase plasma DPA levels by at least about 110%, 120%, even at least about 125% above pre-treatment levels.

In a series of embodiments, the capsular dosage form is administered in an amount and for a duration effective to reduce arachidonic acid (AA) concentration in plasma by at least about 5% below pre-treatment levels. In certain embodiments, the capsular dosage form is administered in an amount and for a duration effective to reduce arachidonic (AA) concentration in plasma by at least about 6%, 7%, 8%, 9%, 10%, even at least about 11%, 12%, 13%, 14%, even at least about 15%, 16%, 17%, 18%, 19%, 20%, or 21%, 22%, 23%, 24% even at least about 25% below pre-treatment levels.

In certain embodiments, the capsular dosage form is administered in an amount, and for a duration, effect to reduce plasma arachidonic acid concentration by at least about 25 µg/mL. In some embodiments, the capsular dosage form is administered in an amount and for a duration sufficient to reduce plasma AA levels by at least about 50 µg/mL, 55 µg/mL, 60 µg/mL, 65 µg/mL, even at least about 70 µg/mL, 75 µg/mL, 80 µg/mL, 85 µg/mL, 90 µg/mL, even at least about 95 µg/mL or 100 µg/mL.

In various embodiments, the capsular dosage form described herein is administered in unit dosage forms as described above.

In various embodiments, the capsular dosage form is administered in an amount of at least about 1 g per day. In some embodiments, the capsular dosage form is administered to provide the PUFA composition in an amount of at least about 2 g/day. In certain embodiments, the capsular dosage form is administered to provide the PUFA composition in an amount of at least about 3 g/day. In particular embodiments, the capsular dosage form is administered to provide the PUFA composition in an amount of at least about 4 g/day. In typical embodiments, the capsular dosage form is administered to provide the PUFA composition in an amount of about 2 g/day. In certain embodiments, the capsular dosage form is administered to provide the PUFA composition in an amount of about 3 g/day or about 4 g per day.

Treatment to Lower Serum or Plasma ApoCIII Levels

Methods are also provided for decreasing a patient's serum or plasma ApoCIII levels, without regard to the patient's pre-treatment plasma triglyceride levels. The methods comprise administering the capsular dosage form described herein to a patient in need of lower ApoCIII levels, in an amount and for duration sufficient to decrease the patient's serum or plasma ApoCIII levels. In typical embodiments, the patient is at risk for cardiovascular heart disease.

In certain embodiments, the capsular dosage form is administered to provide the PUFA composition in an amount and for a duration sufficient to decrease ApoCIII levels by at least about 1%, 2%, 3%, 4%, 5%, 6%, 7%, even at least about 8%, 9% or 10% below pre-treatment levels.

Other Methods of Treatment

In certain aspects, the disclosure provides methods of treating subjects who display healthy levels of triglycerides but would benefit from prophylactic treatment with a PUFA composition. For example, a subject may have healthy levels of triglycerides but may have other risk factors for cardiovascular disease such as a family history of heart disease, obesity, diabetes or lifestyle choices such as tobacco use which puts the subject at risk for cardiovascular disease. In certain embodiments, a subject with plasma triglyceride levels of about 500 mg/dL or less, such as about 400 mg/dL or less, such as about 300 mg/dL or less, such as about 200 mg/dL or less, such as about 100 mg/dL or less may be treated with the capsular dosage form, such as a prophylactic dosage of the capsular dosage form.

In another aspect, the capsular dosage form described herein is used to treat other disorders, including one or more of nonalcoholic steatohepatitis (NASH), hyperlipoproteinemia, including but not limited to type III hyperlipoproteinemia, and metabolic syndrome. In another aspect, the capsular dosage form described herein is used to treat atherogenic/diabetic/mixed dyslipidemia.

In certain embodiments, the capsular dosage form is administered to children of less than 18 years of age, such as between 5 or 6 and 18 years, such as between 10 and 18 years of age, such as between 5 or 6 and 10 years of age. In such embodiments, the capsular dosage form may be administered in order to lower triglycerides, for example in patients with refractory high triglycerides, not controlled by diet and statins alone, or in whom statins are not indicated.

The capsular dosage form described herein may also be useful to lower triglyceride levels in patients with a genetic pre-disposition to raised triglyceride levels. One example of such a genetic condition is familial chylomicronemia.

The capsular dosage form may be administered for the treatment of non-alcoholic steatohepatitis (NASH), in pediatric populations such as those with the age ranges described above or in adults.

The capsular dosage may be administered for the treatment of cystic fibrosis, in pediatric populations such as those with the age ranges described above or in adults (see for example "Omega-3 fatty acids for cystic fibrosis (Review)", Oliver and Watson, The Cochrane Library, 2013, Issue 11). In one aspect, the capsular dosage form may be used for the treatment of cystic fibrosis in those patients who also have pancreatic exocrine insufficiency.

The capsular dosage may be administered for the treatment of traumatic head injury, in pediatric populations such as those with the age ranges described above (for example arising out of sporting injuries) or in adults; see for example J Am Coll Nutr. 2015; 34 Suppl 1:60-1.

In certain embodiments, the capsular dosage form is used to reduce resistance to platelet aggregation inhibitors, such as Plavix, including use in the methods described in U.S. patent application Ser. No. 13/620,312, the disclosure of which is incorporated herein by reference in its entirety.

Additional methods of treating and diagnosis employing the capsular dosage forms described herein can be found in U.S. Provisional Patent Application No. 62/069,651, the entire contents of which are incorporated by reference herein.

In another aspect, there is provided a unit dosage form as described in any embodiment or aspect herein for use as a medicament.

In one aspect, there is provided a method of treating severe hypertriglyceridemia comprising administering to a patient in need thereof the unit dosage form as described in any embodiment or aspect herein, in an amount and for a duration sufficient to treat severe hypertriglyceridemia.

In another aspect, there is provided a unit dosage form as described in any embodiment or aspect herein for use as a medicament for the treatment of severe hypertriglyceridemia.

In another aspect, there is provided a plurality of millicapsules as described in any embodiment or aspect herein for use in the manufacture of a medicament for the treatment of severe hypertriglyceridemia.

In one aspect, there is provided a method of treating mixed dyslipidemia comprising administering to a patient in need thereof the unit dosage form as described in any embodiment or aspect herein, in an amount and for a duration sufficient to treat mixed dyslipidemia.

In another aspect, there is provided a unit dosage form as described in any embodiment or aspect herein for use as a medicament for the treatment of mixed dyslipidemia.

In another aspect, there is provided a plurality of millicapsules as described in any embodiment or aspect herein for use in the manufacture of a medicament for the treatment of mixed dyslipidemia.

In one aspect, there is provided a method of treating cystic fibrosis comprising administering to a patient in need thereof the unit dosage form as described in any embodiment or aspect herein, in an amount and for a duration sufficient to treat cystic fibrosis, particularly in pediatric patients.

In another aspect, there is provided a unit dosage form as described in any embodiment or aspect herein for use as a medicament for the treatment of cystic fibrosis, particularly in pediatric patients.

In another aspect, there is provided a plurality of millicapsules as described in any embodiment or aspect herein for use in the manufacture of a medicament for the treatment of cystic fibrosis, particularly in pediatric patients.

In one aspect, there is provided a method of treating NASH comprising administering to a patient in need thereof the unit dosage form as described in any embodiment or aspect herein, in an amount and for a duration sufficient to treat NASH.

In another aspect, there is provided a unit dosage form as described in any embodiment or aspect herein for use as a medicament for the treatment of NASH.

In another aspect, there is provided a plurality of millicapsules as described in any embodiment or aspect herein for use in the manufacture of a medicament for the treatment of NASH.

In one aspect, there is provided a method of treating hyperlipoproteinemia comprising administering to a patient in need thereof the unit dosage form as described in any embodiment or aspect herein, in an amount and for a duration sufficient to treat hyperlipoproteinemia.

In another aspect, there is provided a unit dosage form as described in any embodiment or aspect herein for use as a medicament for the treatment of hyperlipoproteinemia.

In another aspect, there is provided a plurality of millicapsules as described in any embodiment or aspect herein for use in the manufacture of a medicament for the treatment of hyperlipoproteinemia.

In one aspect, there is provided a method of treating treatment of traumatic head injury comprising administering to a patient in need thereof the unit dosage form as described in any embodiment or aspect herein, in an amount and for a duration sufficient to treat treatment of traumatic head injury.

In another aspect, there is provided a unit dosage form as described in any embodiment or aspect herein for use as a medicament for the treatment of treatment of traumatic head injury.

In another aspect, there is provided a plurality of millicapsules as described in any embodiment or aspect herein for use in the manufacture of a medicament for the treatment of treatment of traumatic head injury.

Methods of Manufacture

In another aspect, methods are provided for manufacturing the capsular dosage form described in above.

Manufacturing Uncoated Millicapsules

As discussed above, in some embodiments, the millicapsules used in the unit dosage forms are uncoated. FIG. 1 provides an exemplary flow diagram of a manufacturing process for unit dosage forms comprising uncoated gelatin millicapsules according to a particular embodiment. Stage 1 involves mixing of the PUFA composition with a solvent. Stage 2 involves mixing gelatin and optional excipients as well as solvents, followed by stirring and heating under reduced pressure to promote dissolution and degassing. In Stage 3, the fill from Stage 1 and the gelatin solution from Stage 2 are combined in a liquid manufacturing aid to form the gelatin millicapsules, which are then placed in cold storage in Stage 4. For Stage 5, after separation of the millicapsules from the manufacturing aid, e.g., by centrifugation, the millicapsules may be treated with an emulsifying agent and optional additional solvent followed by drying. After drying, in Stage 6, the capsules may be treated further with emulsifying agent, washed, and then dried again. In Stage 7, the millicapsules are then distributed into unit doses and filled into individual packaging (e.g., sachets, packets, stick-packs, or blisters).

Manufacturing Coated Millicapsules

Figure 2A:
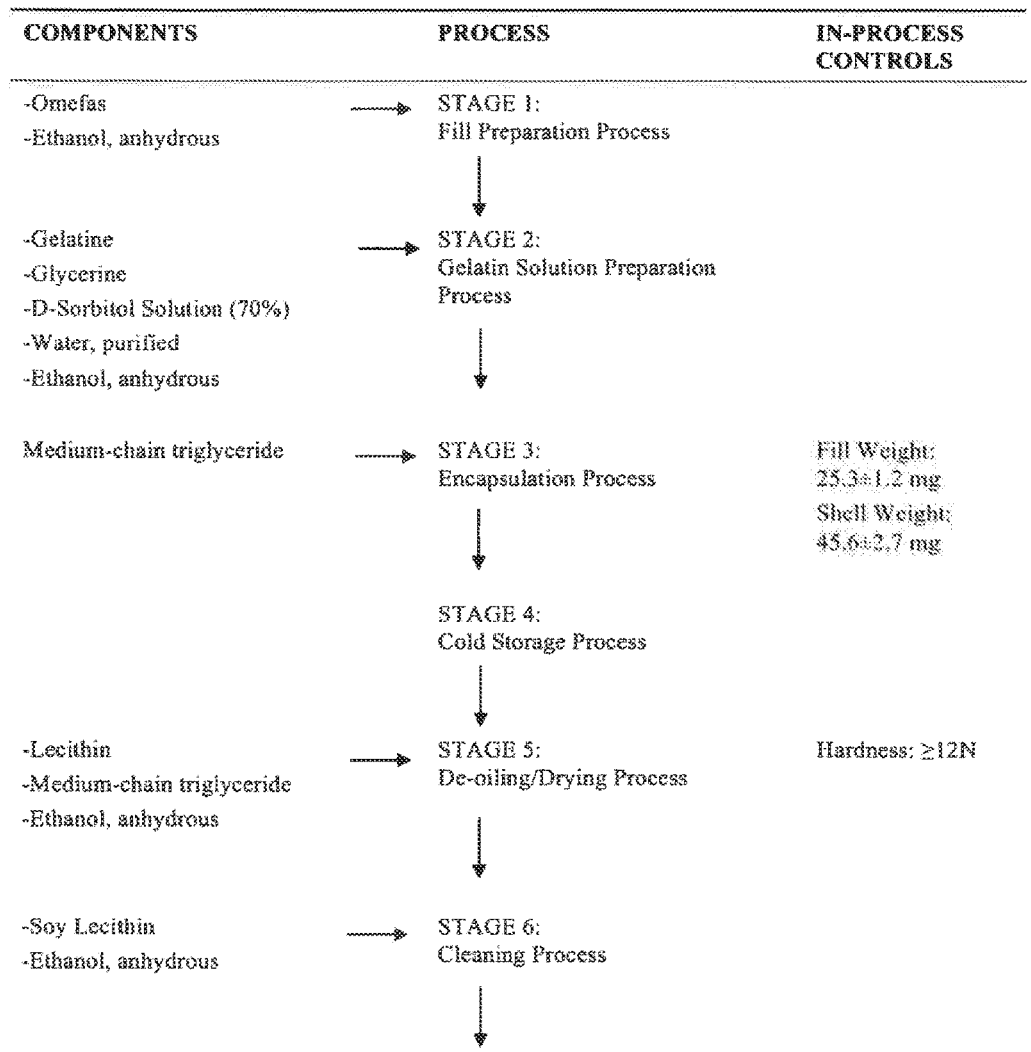

As discussed above, in certain embodiments, the millicapsules used in the unit dosage forms are coated. FIGS. 2A-B provide an exemplary flow diagram of a manufacturing process for unit dosage forms comprising coated gelatin millicapsules according to a particular embodiment. Stage 1 involves mixing of the PUFA composition with a solvent. Stage 2 involves mixing gelatin and optional excipients as well as solvents, followed by stirring and heating under reduced pressure to promote dissolution and degassing. In Stage 3, the fill from Stage 1 and the gelatin solution from Stage 2 are combined in a liquid manufacturing aid to form the gelatin millicapsules, which are then placed in cold storage in Stage 4. For Stage 5, after separation of the millicapsules from the manufacturing aid, e.g., by centrifugation, the millicapsules may be treated with an emulsifying agent and optional additional solvent followed by drying. After drying, in Stage 6, the capsules may be treated further with emulsifying agent, washed, and then dried again. In Stage 7, coating material and excipients are then dissolved or suspended in solution and mixed before spraying onto the millicapsules followed by drying. In Stage 8, an optional anti-tacking agent (e.g., talc, magnesium stearate) may be applied. And in Stage 9, the millicapsules are then distributed into unit doses and filled into individual packaging (e.g., sachets, packets, stick-packs, or blisters).

In one aspect, the coating is applied to the millicapsules in a fluid bed coater or pan coater.

Bioavailability Clinical Trial

Example 3 describes a clinical trial to assess the relative bioavailability of various unit dosage forms described herein (e.g., comprising a plurality of millicapsules containing a PUFA composition therein) and to compare to a reference unit dosage form comprising a single capsule containing the PUFA composition therein.

In certain embodiments, the unit dosage forms comprising a plurality of millicapsules exhibit increased bioavailability of the PUFA composition relative to the single capsule reference unit dosage form. For example, one or more of the millicapsule unit dosage forms may exhibit up to a 5%, 7%, 10%, 12%, 15%, 17%, 20%, 25%, 35%, 50%, 75%, or 100% increase in bioavailability of the PUFA composition relative to the single capsule reference unit dosage form. In some embodiments, the PUFA composition is that used in Epanova®.

In some embodiments, the unit dosage forms comprising a plurality of millicapsules exhibit substantially similar bioavailability of the PUFA composition relative to the single capsule reference unit dosage form. For example, one or more of the millicapsule unit dosage forms may exhibit bioavailability of the PUFA composition that is within about 1, 2, 3, 4, 5, 7, 10, 12, 15, 20, or 25% or less relative to the single capsule reference unit dosage form. In some embodiments, the PUFA composition is that used in Epanova®.

Bioavailability of EPA

In some embodiments, wherein the PUFA composition is selected from that used in Epanova®, the unit dosage forms comprising a plurality of millicapsules exhibit increased bioavailability of EPA relative to the single capsule reference unit dosage form. For example, one or more of the millicapsule unit dosage forms may exhibit up to a 5%, 7%, 10%, 12%, 15%, 17%, 20%, 25%, 35%, 50%, 75%, or 100% increase in bioavailability of EPA relative to the single capsule reference unit dosage form.

For example, one or more of the millicapsule unit dosage forms may exhibit up to a 5%, 7%, 10%, 12%, 15%, 17%, 20%, 25%, 35%, 50%, 75%, or 100% increase in the Area Under the Curve ("AUC") (e.g., $AUC_t$ or $AUC_\infty$) of EPA relative to the single capsule reference unit dosage form. In another example, one or more of the millicapsule unit dosage forms may exhibit up to a 5%, 7%, 10%, 12%, 15%, 17%, 20%, 25%, 35%, 50%, 75%, or 100% increase in the $C_{max}$ of EPA relative to the single capsule reference unit dosage form.

In some embodiments, wherein the PUFA composition is selected from that used in Epanova®, the unit dosage forms comprising a plurality of millicapsules exhibit substantially similar bioavailability of EPA relative to the single capsule reference unit dosage form. For example, one or more of the millicapsule unit dosage forms may exhibit bioavailability of EPA that is within about 1, 2, 3, 4, 5, 7, 10, 12, 15, 20, or 25% or less relative to the single capsule reference unit dosage form.

For example, one or more of the millicapsule unit dosage forms may exhibit AUC for EPA that is within about 1, 2, 3, 4, 5, 7, 10, 12, 15, 20, or 25% or less relative to the single capsule reference unit dosage form. In another example, one or more of the millicapsule unit dosage forms may exhibit $C_{max}$ for EPA that is within about 1, 2, 3, 4, 5, 7, 10, 12, 15, 20, or 25% or less relative to the single capsule reference unit dosage form.

Bioavailability of DHA

In some embodiments wherein the PUFA composition is selected from that used in Epanova®, the unit dosage forms comprising a plurality of millicapsules exhibit increased bioavailability of DHA relative to the single capsule reference unit dosage form. For example, one or more of the millicapsule unit dosage forms may exhibit up to a 5%, 7%, 10%, 12%, 15%, 17%, 20%, 25%, 35%, 50%, 75%, or 100% increase in bioavailability of DHA relative to the single capsule reference unit dosage form.

For example, one or more of the millicapsule unit dosage forms may exhibit up to a 5%, 7%, 10%, 12%, 15%, 17%, 20%, 25%, 35%, 50%, 75%, or 100% increase in the AUC (e.g., $AUC_t$ or $AUC_\infty$) of DHA relative to the single capsule reference unit dosage form. In another example, one or more of the millicapsule unit dosage forms may exhibit up to a 5%, 7%, 10%, 12%, 15%, 17%, 20%, 25%, 35%, 50%, 75%, or 100% increase in the $C_{max}$ of DHA relative to the single capsule reference unit dosage form.

In some embodiments, wherein the PUFA composition is selected from that used in Epanova®, the unit dosage forms comprising a plurality of millicapsules exhibit substantially similar bioavailability of DHA relative to the single capsule reference unit dosage form. For example, one or more of the millicapsule unit dosage forms may exhibit bioavailability of DHA that is within about 1, 2, 3, 4, 5, 7, 10, 12, 15, 20, or 25% or less relative to the single capsule reference unit dosage form.

For example, one or more of the millicapsule unit dosage forms may exhibit AUC for DHA that is within about 1, 2, 3, 4, 5, 7, 10, 12, 15, 20, or 25% or less relative to the single capsule reference unit dosage form. In another example, one or more of the millicapsule unit dosage forms may exhibit $C_{max}$ for DHA that is within about 1, 2, 3, 4, 5, 7, 10, 12, 15, 20, or 25% or less relative to the single capsule reference unit dosage form.

Bioavailability of DPA

In some embodiments wherein the PUFA composition is that used in Epanova®, the unit dosage forms comprising a plurality of millicapsules exhibit increased bioavailability of DPA relative to the single capsule reference unit dosage form. For example, one or more of the millicapsule unit dosage forms may exhibit up to a 5%, 7%, 10%, 12%, 15%, 17%, 20%, 25%, 35%, 50%, 75%, or 100% increase in bioavailability of DPA relative to the single capsule reference unit dosage form.

For example, one or more of the millicapsule unit dosage forms may exhibit up to a 5%, 7%, 10%, 12%, 15%, 17%, 20%, 25%, 35%, 50%, 75%, or 100% increase in the AUC (e.g., $AUC_t$ or $AUC_\infty$) of DPA relative to the single capsule reference unit dosage form. In another example, one or more of the millicapsule unit dosage forms may exhibit up to a 5%, 7%, 10%, 12%, 15%, 17%, 20%, 25%, 35%, 50%, 75%, or 100% increase in the $C_{max}$ of DPA relative to the single capsule reference unit dosage form.

In some embodiments, wherein the PUFA composition is that used in Epanova®, the unit dosage forms comprising a plurality of millicapsules exhibit substantially similar bioavailability of DPA relative to the single capsule reference unit dosage form. For example, one or more of the millicapsule unit dosage forms may exhibit bioavailability of DPA that is within about 1, 2, 3, 4, 5, 7, 10, 12, 15, 20, or 25% or less relative to the single capsule reference unit dosage form.

For example, one or more of the millicapsule unit dosage forms may exhibit AUC for DPA that is within about 1, 2, 3, 4, 5, 7, 10, 12, 15, 20, or 25% or less relative to the single capsule reference unit dosage form. In another example, one or more of the millicapsule unit dosage forms may exhibit $C_{max}$ for DPA that is within about 1, 2, 3, 4, 5, 7, 10, 12, 15, 20, or 25% or less relative to the single capsule reference unit dosage form.

Patient Compliance and Side Effect Profile

In certain embodiments, in addition to exhibiting increased or substantially similar bioavailability, the unit dosage forms comprising a plurality of millicapsules of the PUFA composition may exhibit improved performance in patient compliance or an improved side effect profile relative to the single capsule reference unit dosage form. In some such embodiments, the PUFA composition is selected from that used in Epanova®.

For instance, in some embodiments, unit dosage forms comprising a plurality of millicapsules score higher on taste or odor tests relative to the single capsule reference unit dosage form, which may lead to improved patient compliance relative to the single capsule reference unit dosage form. In other embodiments, unit dosage forms comprising a plurality of millicapsules score similarly in taste or odour tests relative to the single capsule reference unit dosage form. In still more embodiments, unit dosage forms comprising a plurality of millicapsules score slightly worse in taste or odour tests relative to the single capsule reference unit dosage form. In some embodiments, fewer than 30%, such as fewer than 40%, such as fewer than 50%, such as fewer than 60%, such as fewer than 70% of subjects receiving the millicapsules described them as having a fishy taste and/or odour.

In other embodiments, unit dosage forms comprising a plurality of millicapsules produce fewer incidents of side effects (such as belching, foul breath or aftertaste, heartburn, nausea or upset stomach, loose stools or diarrhea, abdominal pain, rash, and nosebleeds) relative to the single capsule reference unit dosage form. Reduction in the incidence of such side effects may lead to improved patient compliance relative to the single capsule reference unit dosage form.

Other aspects include 1 to 18 as follows:

1. A unit dosage form comprising a plurality of millicapsules containing a polyunsaturated free fatty acid (PUFA) composition substantially in free acid form, wherein the millicapsules are soft gelatin capsules comprising porcine Type A gelatin.

2. The dosage form of aspect 1, wherein the PUFA composition is that used in Epanova®.

3. The dosage form of aspect 1 comprising about 1500 mg to about 2500 mg of the PUFA composition.

4. The dosage form of aspect 3 comprising about 2000 mg of the PUFA composition.

5. The dosage form of aspect 1 comprising about 500 mg to about 1500 mg of the PUFA composition.

6. The dosage form of aspect 5 comprising about 1000 mg of the PUFA composition.

7. The dosage form of aspect 1 comprising about 40 to about 200 millicapsules.

8. The dosage form of aspect 7 comprising about 80 millicapsules.

9. The dosage form of aspect 1, wherein the millicapsules are uncoated.

10. The dosage form of aspect 1, wherein the millicapsules are coated.

11. The dosage form of aspect 13, wherein the millicapsules are coated with a poly(ethylacrylate-methylacrylate) copolymer.

12. The dosage form of aspect 13, wherein the millicapsules have a weight ratio of PUFA composition to coating of about 10:1 to about 25:1.

13. The dosage form of aspect 13, wherein the millicapsules have a weight ratio of PUFA composition to coating of about 25:1 to about 50:1.

14. The dosage form of aspect 1, wherein the millicapsules are approximately seamless.

15. The dosage form of aspect 1, wherein the millicapsules are approximately spherical in shape and include a diameter from about 5 to about 3 mm.

16. The dosage form of aspect 1, wherein each millicapsule contains about 15 to about 50 mg of the PUFA composition.

17. A method of treating severe hypertriglyceridemia comprising administering to a patient in need thereof the unit dosage form of aspect 1 in an amount and for a duration sufficient to treat severe hypertriglyceridemia.

18. The dosage form of aspect 1 wherein said dosage form is a sachet.

EXAMPLES

Example 1: Unit Dosage Forms of a Plurality of Millicapsules Containing the Epanova® PUFA Composition Three different types of unit dosage forms were prepared (A, B, and C), each comprising about 2000 mg of the PUFA composition of Epanova® ("Omefas" or "omega-3 carboxylic acids") in about 80 soft gelatin millicapsules of about 4 mm in diameter. Unit dosage form A was uncoated, while unit dosage forms B and C were coated. Each unit dosage form was individually packaged in a sachet made from an aluminum laminate. Table 1 lists the compositions of each of the prepared unit dosage forms:

TABLE 1

| | Quantity (mg per sachet) | | | |
| Component | A (uncoated) | B (Coat 1) | C (Coat 2) | Function |
| --- | --- | --- | --- | --- |
| Gelatin millicapsule | | | | |
| Omefas | 2000 | 2000 | 2000 | Active substance |
| Gelatin (porcine skin type A, 200 bloom) and plasticizer mix (glycerin and sorbitol 70%) | approximately 900 | approximately 900 | approximately 900 | Capsule core |

TABLE 1-continued

| | Quantity (mg per sachet) | | | |
| Component | A (uncoated) | B (Coat 1) | C (Coat 2) | Function |
| --- | --- | --- | --- | --- |
| Coating | | | | |
| Carboxymethyl-cellulose sodium | NA | 1.6 | 2.7 | Viscosity enhancer |
| Iron oxide yellow | NA | 1.0 | 1.6 | Color |
| Talc | NA | 90 | 120 | Filler |
| Titanium dioxide | NA | 18 | 29 | Color |
| Polysorbate 80 | NA | 1.6 | 2.7 | Emulsifying agent |
| Poly(ethyl acrylate, methylmethacrylate) 2:1 provided as NM30D | NA | 52 | 110 | Film former |
| Water | NA | As needed | As needed | Solvent |
| Final mix | | | | |
| Talc | NA | 3.1 | 3.2 | Anti-tacking agent |

NA = Not applicable

Coat 1 (Formulation B) results in the coating representing about 5% of the final capsule weight. Coat 2 (Formulation C) results in the coating representing about 8% of the final capsule weight. Eudragit® NM30D was used (Evonik Industries, Poly(ethylacrylate, methylmethacrylate) 2:1, weight average molar mass: approx. 600,000 g/mol; NM30D also contains Brij®78P surfactant, the main component of which is polyethylene glycol octadecyl ether).

Example 2: Manufacturing Processes for Unit Dosage Forms of a Plurality of Millicapsules Containing the Epanova® PUFA Composition Manufacturing Process for Unit Dosage Forms of a Plurality of Uncoated Millicapsules FIG. 1 provides a flow diagram of a manufacturing process for unit dosage forms comprising uncoated gelatin millicapsules according to a particular embodiment.

Stage 1: Fill Preparation Process. The Epanova® PUFA Composition ("Omefas") and anhydrous ethanol are mixed in inert atmosphere (nitrogen).

Stage 2: Gelatin Solution Preparation Process. Gelatin, Glycerin, D-Sorbitol Solution (70%), purified water, and anhydrous ethanol are mixed and then stirred such that the mixture is dissolved and degassed.

Stage 3: Encapsulation Process. The fill from Stage 1 and the gelatin solution from Stage 2 are dropped into the circulating liquid, medium-chain triglyceride (MCT), through an encapsulation machine to form the soft gelatin millicapsules.

Stage 4: Cold Storage Process. The soft millicapsules formed in Stage 3 are stored in a cool storage.

Stage 5: De-oiling/Drying Process. The millicapsules produced in Stage 4 are separated from the circulated liquid by centrifugation. During the centrifugation process the millicapsules are sprayed with emulsifier and finally sprayed with ethanol. After the centrifugation process the millicapsules are dried.

Stage 6: Cleaning Process. The dried millicapsules are washed with ethanol based emulsifying solution. The washing liquid is discharged and the millicapsules are further dried.

Stage 7: Sachet filling. The millicapsules are dispensed into aluminum sachets.

Manufacturing Process for Unit Dosage Forms of a Plurality of Coated Millicapsules FIGS. 2A-B provide a flow diagram of a manufacturing process for unit dosage forms comprising coated gelatin millicapsules according to a particular embodiment.

Stage 1: Fill Preparation Process. The Epanova® PUFA Composition ("Omefas") and anhydrous ethanol are mixed in inert atmosphere (nitrogen).

Stage 2: Gelatin Solution Preparation Process. Gelatin, Glycerin, D-Sorbitol Solution (70%), purified water, and anhydrous ethanol are mixed and then stirred such that the mixture is dissolved and degassed.

Stage 3: Encapsulation Process. The fill from Stage 1 and the gelatin solution from Stage 2 are dropped into the circulating liquid, medium-chain triglyceride (MCT), through an encapsulation machine to form the soft gelatin millicapsules.

Stage 4: Cold Storage Process. The soft millicapsules formed in Stage 3 are stored in a cool storage.

Stage 5: De-oiling/Drying Process. The millicapsules produced in Stage 4 are separated from the circulated liquid by centrifugation. During the centrifugation process the millicapsules are sprayed with emulsifier and finally sprayed with ethanol. After the centrifugation process the millicapsules are dried.

Stage 6: Cleaning Process. The dried millicapsules are washed with ethanol based emulsifying solution. The washing liquid is discharged and the millicapsules are further dried.

Stage 7: Capsule coating. Talc, Titanium dioxide, Iron oxide yellow, Carboxymethylcellulose sodium, Polysorbate 80 and Poly(ethyl acrylate, methylmethacrylate) 2:1 are suspended in water. The suspension is homogenized using a suitable mixer. The suspension is sprayed onto the millicapsules in a fluid bed coater during continues drying.

Stage 8: Final mixing. The coated millicapsules are mixed with Talc in a suitable mixer.

Stage 9: Sachet filling. The millicapsules are dispensed into aluminum sachets.

Example 3: Bioavailability Clinical Trial

A randomized, open-label, single-center, cross-over study in healthy subjects to assess the relative bioavailability of EPA and DHA delivered by unit dosage forms A, B, and C as described above in relation to the current Epanova® capsule under fasting (Part 1) and fed (Part 2) conditions will be performed.

Study Rationale

The purpose with the study is to compare the pharmacokinetics (PK) of three different capsule formulations ("Omefas" or "omega-3-carboxylic acids" test formulations A, B, and C) with Epanova® capsules 1000 mg under fasted and fed conditions in a two-part study.

Study Objectives

The objective of this study is to assess the relative bioavailability of different capsule formulations containing omega-3-carboxylic acids (test formulations A, B, and C) in relation to Epanova® capsules 1000 mg (reference formulation).

Primary Objective. To assess the relative bioavailability of the different omega-3-carboxylic acids capsule formulations in relation to Epanova® capsules 1000 mg.

Secondary Objectives. To characterize and compare the plasma PK profiles of EPA and DHA when administered as the different formulations and to assess the safety of single doses of Epanova® and the omega-3-carboxylic acids test formulations in healthy subjects.

Exploratory Objective. To assess the taste of Epanova® and the omega-3-carboxylic acids test formulations, using a questionnaire.

Outcome Variables

Pharmacokinetic parameters. Where possible, the PK parameters will be assessed for EPA and DHA on baseline subtracted plasma concentrations.

Primary PK parameters: AUC, $AUC_{(0-72)}$, $C_{max}$

Secondary PK parameters: $AUC_{last}$, $C_0$, $t_{max}$, $t_{1/2}$, $\lambda_z$, $\lambda_z$ Additional PK parameters for diagnostic purposes: $\lambda_z$, Interval, $\lambda_z$, N, Rsq adj, % $AUC_{extrapolated}$ $AUC_{(0-72)}$ and $C_{max}$, as well as $C_0$ of EPA and DHA will also be estimated based on unadjusted plasma concentrations.

Study Design

This study will be a randomized, open-label, cross-over study in healthy male and female (non-childbearing potential) subjects, performed at a single study center. The study is divided into two parts, Part 1 and Part 2.

Part 1

Part 1: Part 1 will be a 4-way (4 treatments, 4 periods) cross-over study to assess the relative bioavailability and to characterize and compare the PK profiles of the three different prototype capsule formulations ("Omefas" or "omega-3-carboxylic acids" test formulation A, B, and C) in relation to Epanova® capsules 1000 mg, under fasted conditions.

Subjects will receive a single dose of each treatment on four occasions, respectively:

| Treatment A | Omega-3-carboxylic acids 2000 mg uncoated capsules (test formulation A) | 2 × 2 g |
| Treatment B | Omega-3-carboxylic acids 2000 mg coated capsules coat 1 (test formulation B) | 2 × 2 g |
| Treatment C | Omega-3-carboxylic acids 2000 mg coated capsules coat 2 (test formulation C) | 2 × 2 g |
| Treatment D | Epanova ® capsules 1000 mg (reference formulation) | 4 × 1 g |

Subjects will be randomized to a 4 sequence Williams design for 4 treatments and 4 periods: ADBC, BACD, CBDA, and DCAB.

Part 1 of the study will comprise: a screening period of maximum 28 days; four treatment periods during which subjects will be resident from 2 days before dosing until 72 hours after dosing; discharged on the morning of Day 4; and a final safety follow-up study visit within 10 to 14 days after the last administration of investigational medical product (IMP).

There will be a washout period of at least 14 days (at least five half-lives) between each dose administration.

The IMP will be administered after an overnight fast of at least 10 hours. Food intake may be resumed 4 hours after dosing. Safety assessments, PK sampling and taste testing will be performed in accordance with the Schedule of Assessments. The taste scores of the IMPs will be assessed using a questionnaire at 1 hour and 4 hours post-dose at each treatment period.

Based on the results obtained in Part 1, two of the three different capsule formulations will be selected to be administered along with Epanova® capsules 1000 mg to Part 2, under fed conditions.

Part 2

Part 2 will be a 3-way (3 treatments, 3 periods) cross-over study to assess the relative bioavailability and to characterize and compare the PK profiles of the two different capsule formulations ("Omefas" or "omega-3-carboxylic acids" test formulation A and B or C) in relation to Epanova® capsules 1000 mg, under fed conditions.

Subjects will receive a single dose of each treatment on three occasions, respectively:

| Treatment A | Omega-3-carboxylic acids 2000 mg uncoated capsules (test formulation A) | 2 × 2 g |
|---|---|---|
| Treatment B | Omega-3-carboxylic acids 2000 mg coated capsules coat 1 (test formulation B) OR Omega-3-carboxylic acids 2000 mg coated capsules coat 2 (test formulation C) | 2 × 2 g |
| Treatment C | Epanova ® capsules 1000 mg (reference formulation) | 4 × 1 g |

Subjects will be randomized to a 6 sequence Williams design for 3 treatments and 3 periods: ABC, BCA, CAB, ACB, BAC, and CBA.

Part 2 of the study will comprise: a screening period of maximum 28 days; three treatment periods during which subjects will be resident from 2 days before dosing until 72 hours after dosing; discharged on the morning of Day 4; and a final safety follow-up study visit within 10 to 14 days after the last administration of IMP.

There will be a washout period of at least 14 days (at least five half-lives) between each dose administration.

On the morning of dosing, subjects will be served breakfast prior to dosing. The IMP will be administered 30 minutes after start of intake of the high-fat, high-calorie breakfast, constituting the ingredients of the regulatory FDA breakfast. Safety assessments, PK sampling and taste testing will be performed in accordance with the Schedule of Assessments. The taste scores of the IMPS will be assessed using a questionnaire at 1 hour and 4 hours post-dose at each treatment period.

Investigational Medicinal Product

| Formulation: | Part 1 Omega-3-carboxylic acids 2000 mg uncoated capsules (test formulation A) Omega-3-carboxylic acids 2000 mg coated capsules coat 1 (test formulation B) Omega-3-carboxylic acids 2000 mg coated capsules coat 2 (test formulation C) Epanova ® capsules 1000 mg (reference formulation) Part 2 Omega-3-carboxylic acids 2000 mg uncoated capsules (test formulation A) Omega-3-carboxylic acids 2000 mg coated capsules coat 1 (test formulation B) OR Omega-3-carboxylic acids 2000 mg coated capsules coat 2 (test formulation C) Epanova ® capsules 1000 mg (reference formulation) Epanova ® capsules 1000 mg is a single unit capsule containing 1 g of omega-3-carboxylic acids. The different prototype capsule formulations comprise multiples of small capsules in a stick-pack. Each stick-pack contains a 2 g dose of omega-3-carboxylic acids. | |
|---|---|---|
| Strength/ Concentrations: | Omega-3-carboxylic acids 2000 mg un-coated capsules (test formulation A) | 2 g |
| | Omega-3-carboxylic acids 2000 mg coated capsules coat 1 (test formulation B) | 2 g |
| | Omega-3-carboxylic acids 2000 mg coated capsules coat 2 (test formulation C) | 2 g |
| | Epanova ® capsules 1000 mg (reference formulation) | 1 g |
| Dose: | 4 g of omega-3-carboxylic acids | |
| Route of administration: | Oral | |
| Regimen: | Single dose | |

Study Duration

Each subject will be involved in the study for approximately 12 weeks if participating in Part 1 and for approximately 10 weeks if participating in Part 2.

Pharmacokinetic Sampling Times and Sample Analysis

Blood samples for the determination of plasma concentrations of total EPA and DHA will be collected for each treatment period: 3 pre-dose samples (−12, −1 and 0 hours; prior to IMP administration) and post-dose at 0.5, 1, 2, 3, 4, 5, 6, 7.5, 9, 12, 24, 36, 48 and 72 hours (17 samples per treatment period).

Samples will be collected, handled, labeled, stored, and shipped as detailed in the Laboratory Manual. Plasma samples will be analyzed for total EPA and DHA using a validated assay.

Pharmacokinetic Data Analysis

The PK analysis set will include all healthy subjects who received at least one dose of test or reference formulation without important protocol deviations or violations thought to significantly affect the PK (e.g., subject vomited, wrong dose administered, prohibited concomitant medication taken).

Plasma PK parameters will be calculated using baseline subtracted concentrations of EPA and DHA. $AUC_{(0-72)}$ and $C_{max}$, as well as $C_0$ of EPA and DHA will also be estimated based on unadjusted plasma concentrations. The baseline concentration will be the arithmetic mean value of the available data from the pre-dose samples for each treatments period (−12 h, −1 h and 0 h prior to IMP administration), applicable to unadjusted and baseline subtracted parameters.

Analyses will be performed using a linear mixed-effects analysis of variance model (ANOVA) using the natural logarithm of AUC, $AUC_{(0-72)}$ and $C_{max}$ as the response variables. The linear mixed-effects model would contain covariates associated with sequence, period and treatment as fixed effects, and subjects nested within sequence as a random effect.

Transformed back from the logarithmic scale, geometric means, together with confidence intervals (CIs) (2-sided 95%) for AUC and $C_{max}$ will be estimated and presented. In addition, ratios of geometric means, together with CIs (2-sided 90%) will be estimated and presented. The analysis described for AUC and $C_{max}$ will also be conducted for $AUC_{(0-72)}$. Data from subjects excluded from the PK analysis set will be included in the data listings, but not in the summaries or statistical analyses.

Results

Part A

Epanova soft gelatin capsules were prepared using Type A porcine gelatin and coated with Eudragit NE-30D (Evonik Industries AG). The capsules contained 545 mg/capsule EPA, 194 mg/capsule DHA, and a total omega-3 fatty acid content of 862 mg/capsule (capsules contained an average of 1002 mg oil).

Millicapsules were prepared using the method described in the Examples above and left uncoated, or coated with Eudragit-NM-30D (Evonik Industries AG) as described above.

The composition of the fatty acid composition (EPA, DHA, EPA+DHA, total omega-3 fatty acids) is evaluated by a gas chromatographic method using a USP G5 column, a temperature gradient and Flame Ionization Detection. Free fatty acids and fatty acid ethyl esters are converted to fatty acid methyl esters prior to chromatographic analysis. Composition is determined by comparison of retention time and quantitation against a suitable standard mixture. The PUFA composition in the millicapsules contained 570 mg/g EPA, 195 mg/g DHA and a total omega-3 fatty acid content of 873 mg/g.

Figure 3:
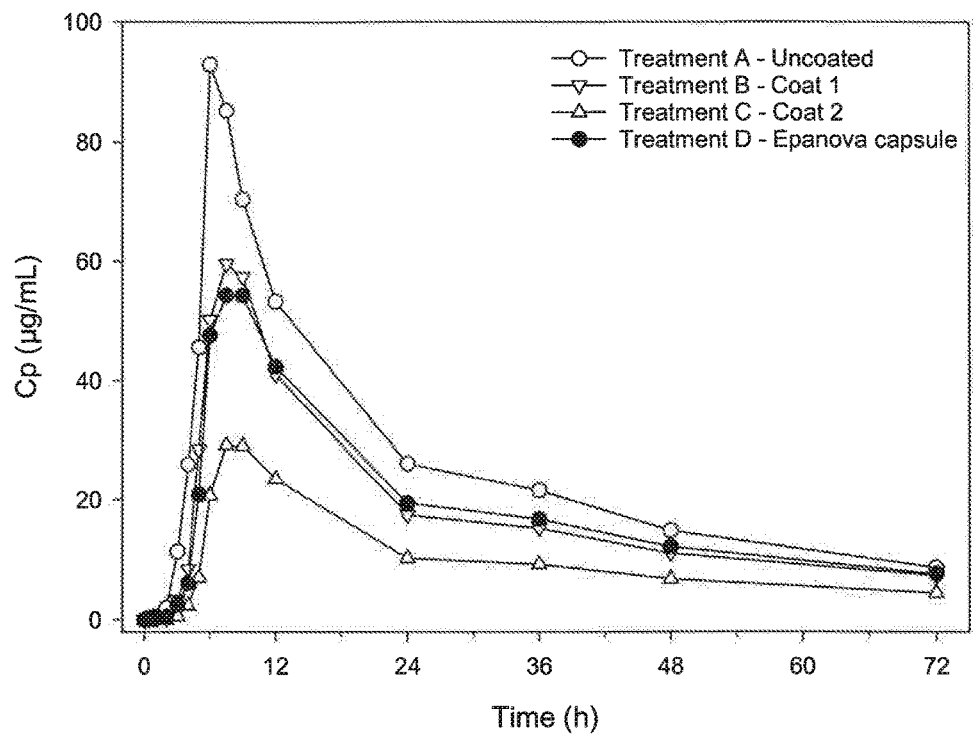
FIG. 3 shows baseline adjusted mean EPA plasma concentration vs time curves for the four treatment groups for Part A of a clinical study described in the Examples.

FIG. 3 shows baseline adjusted mean EPA plasma concentration vs time curves for the four treatment groups:

Treatment A=uncoated millicapsules, Tmax=6 h

Treatment B=coat 1, Tmax=7.5 h

Treatment C=coat 2, Tmax=9.0 h

Treatment D=capsule reference, Tmax=7.5 h

Geomean ratios with 90% confidence interval AUC (0-72 h) and Cmax calculated on baseline adjusted EPA concentrations are set out in the tables below.

Analyte=EPA, PK=AUC-72 (baseline corrected)

|        | N  | Ratios (90% CI)      | P value  | Intra-subject (% CV) | Inter-subject (% CV) |
|--------|----|----------------------|----------|----------------------|----------------------|
| A vs D | 36 | 1.59 (1.29, 1.96)    | 0.0006   | 56.57                | 28.25                |
| B vs D | 37 | 1.00 (0.79, 1.26)    | 0.9830   | 67.11                | 37.53                |
| C vs D | 37 | 0.49 (0.38, 0.64)    | <0.0001  | 76.45                | 50.40                |

Analyte=EPA, PK=Cmax (baseline corrected)

|        | N  | Ratios (90% CI)      | P value  | Intra-subject (% CV) | Inter-subject (% CV) |
|--------|----|----------------------|----------|----------------------|----------------------|
| A vs D | 36 | 1.90 (1.49, 2.43)    | <0.0001  | 68.81                | 35.59                |
| B vs D | 37 | 1.09 (0.84, 1.43)    | 0.5760   | 76.82                | 55.36                |
| C vs D | 37 | 0.50 (0.37, 0.66)    | 0.0002   | 81.43                | 55.45                |

Figure 4:
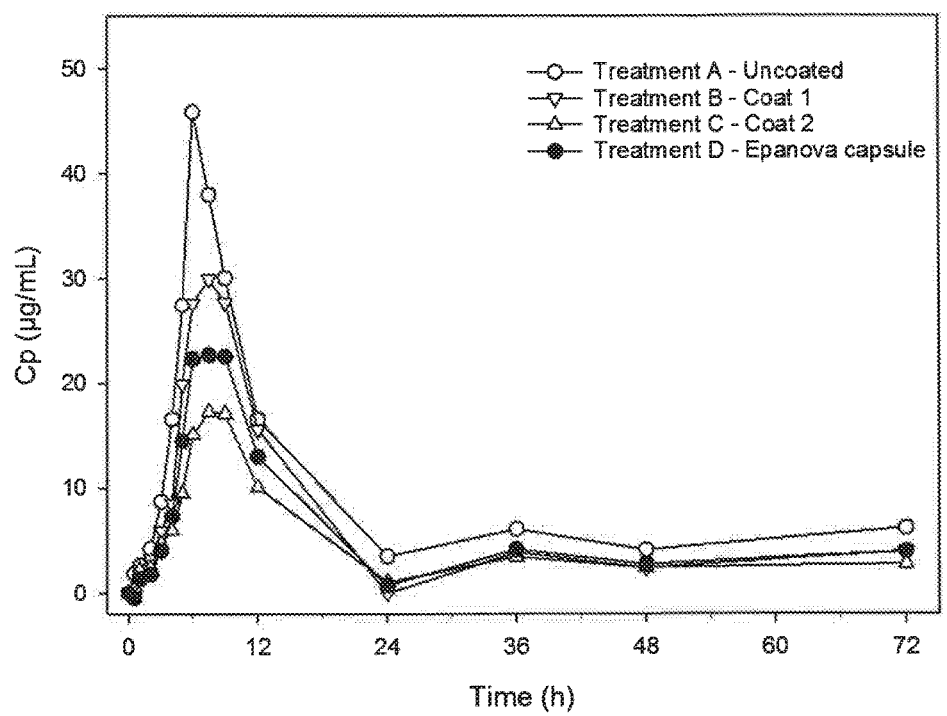
FIG. 4 shows baseline adjusted mean DHA plasma concentration vs time curves for the four treatment groups for Part A of a clinical study described in the Examples.

FIG. 4 shows baseline adjusted mean DHA plasma concentration vs time curves for the four treatment groups:

Treatment A=uncoated millicapsules

Treatment B=coat 1

Treatment C=coat 2

Treatment D=capsule reference

Geomean ratios with 90% confidence interval AUC (0-72 h) and Cmax calculated on baseline adjusted DHA concentrations are set out in the tables below.

Analyte=DHA, PK=AUC-72 (baseline corrected)

| Treatment          | LSMeans (90% CI)         |
|--------------------|--------------------------|
| A (uncoated)       | 581.74 (472.56, 716.14)  |
| B (coat 1)         | 399.14 (321.16, 496.06)  |
| C (coat 2)         | 297.08 (233.09, 378.63)  |
| D (standard capsule) | 347.88 (283.05, 427.56) |

|        | N  | Ratios (90% CI)      | P value | Intra-subject (% CV) | Inter-subject (% CV) |
|--------|----|----------------------|---------|----------------------|----------------------|
| A vs D | 36 | 1.65 (1.29, 2.12)    | 0.0017  | 69.99                | 45.65                |
| B vs D | 37 | 1.14 (0.87, 1.48)    | 0.4238  | 76.77                | 46.64                |
| C vs D | 37 | 0.84 (0.65, 1.09)    | 0.2695  | 73.32                | 63.75                |

Analyte=DHA, PK=Cmax (baseline corrected)

| Treatment          | LSMeans (90% CI)      |
|--------------------|-----------------------|
| A (uncoated)       | 46.99 (39.99, 55.23)  |
| B (coat 1)         | 30.98 (25.90, 37.07)  |
| C (coat 2)         | 18.60 (15.39, 22.48)  |
| D (standard capsule) | 23.75 (20.16, 27.98) |

|        | N  | Ratios (90% CI)      | P value | Intra-subject (% CV) | Inter-subject (% CV) |
|--------|----|----------------------|---------|----------------------|----------------------|
| A vs D | 36 | 1.95 (1.61, 2.37)    | <0.0001 | 51.66                | 35.42                |
| B vs D | 37 | 1.30 (1.06, 1.60)    | 0.0371  | 56.50                | 43.21                |
| C vs D | 37 | 0.78 (0.63, 0.96)    | 0.0475  | 56.39                | 46.41                |

The results above show that Treatment B, millicapsules with the thinner coat 1 of 5% of the total capsule weight, were nearest in bioequivalence to the standard Epanova capsules (treatment D), so these were used as the coated formulation in Part B of the study.

Part B

Figure 5:
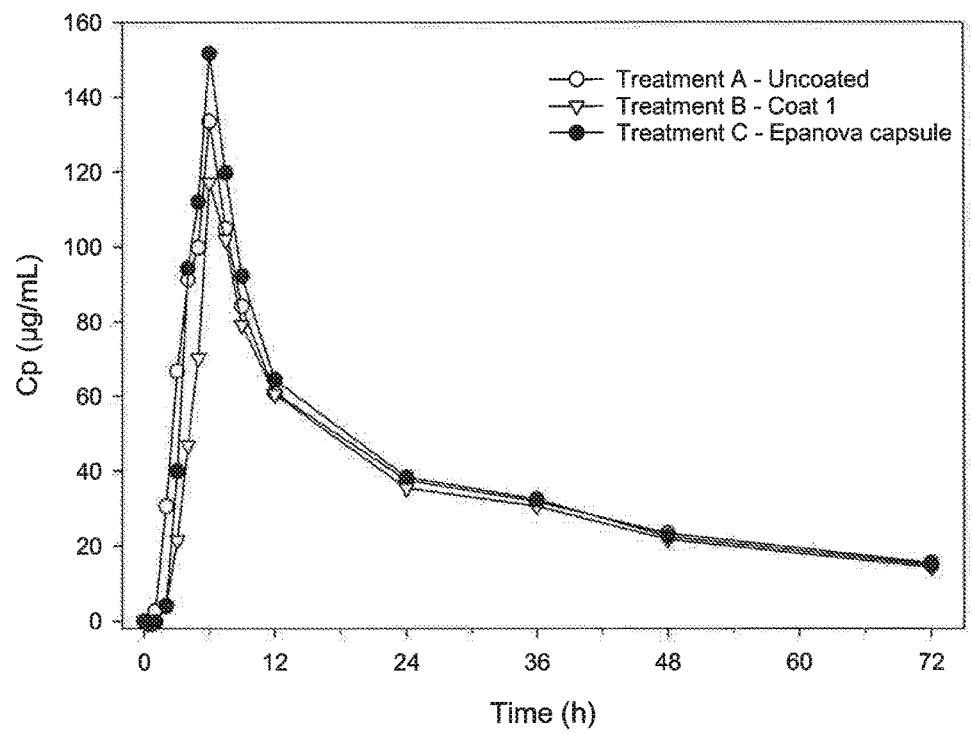
FIG. 5 shows baseline adjusted mean EPA plasma concentration vs time curves for the four treatment groups for Part B of a clinical study described in the Examples.
Figure 6:
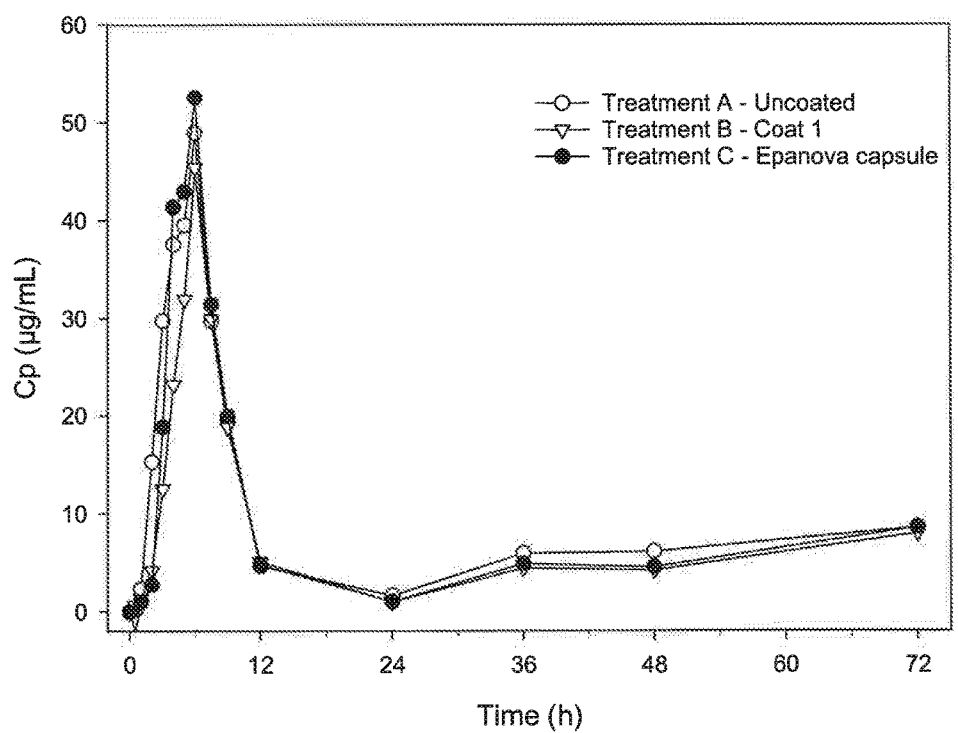
FIG. 6 shows baseline adjusted mean DHA plasma concentration vs time curves for the four treatment groups for Part B of a clinical study described in the Examples.

FIGS. 5 and 6 show EPA and DHA concentrations over time for Part B of the study.

Treatment A: Uncoated seamless capsules (sachet)

Treatment B: Coated (#1) seamless capsules (sachet)

Treatment C: Reference-Epanova Mono capsule

EPA Concentration

|         | $T_{max}$ (h) | Ratio & 90% CI | |
|---------|---------------|----------------|---|
|         |               | $C_{max}$      | $AUC_{0-72\,h}$ |
| B vs C  | 6.7           | 0.76 (0.7-0.83) | 0.88 (0.85-0.92) |
| C (ref) | 5.7           |                |   |

DPA Concentration

|         | $T_{max}$ (h) | Ratio & 90% CI | |
|---------|---------------|----------------|---|
|         |               | $C_{max}$      | $AUC_{0-72\,h}$ |
| B vs C  | 6.6           | 0.78 (0.69-0.89) | 0.90 (0.78-1.05) |
| C (ref) | 5.1           |                |   |

Taste Questionnaire

Trial participants in part A of the study were asked the question:

"Do you think this medication has a fishy taste?" at 1 hour after dosing and 4 hours after dosing.

The answers showed there was little or no significant difference between the three millicapsule formulations (uncoated or two different coat thickness) with about half of participants finding a fishy taste at both time points (see table below). Fewer (7/37) of the participants receiving the mono-capsule reference reported a fishy taste at 1 hour but this increased to 14/37 by 4 hours.

| Formulation | 1 hour - number who reported fishy taste (total participants) | 4 hour - number who reported fishy taste (total participants) |
| --- | --- | --- |
| Uncoated | 17 (37) | 15 (37) |
| Coat 1 | 22 (40) | 23 (40) |
| Coat 2 | 17 (37) | 17 (37) |

Conclusions

Firstly, Treatment B, millicapsules with the thinner coat 1 of about 5% total capsule weight, were nearest in bioequivalence to the standard Epanova capsules (treatment D).

Secondly, Treatment A, the uncoated millicapsules gave a surprisingly high Cmax, and so a higher absorption of the omega-3 fatty acids into the bloodstream. This increased absorption potentially allows for a smaller dose of fatty acid composition to be administered, which the skilled person will understand may be desirable for several reasons, including those of benefit to the patient (such as potential reduction in gastric side effects) and others of economic and social benefit (reduction in cost, reduction in number of fish caught to supply the oil used to make the composition).

Thirdly, the absence of a coat on the millicapsules did not appear to adversely affect the aftertaste of the medicine.

Example 4: Stability Studies

The batches of millicapsules (uncoated and coat #1 (treatment B)) used in the clinical study described in Example 3 were stored at 25° C./60% RH for up to 12 months and at 40° C./75% RH for up to 6 months, in 2 g amounts in aluminium sachets, and their stability assessed.

The results for glyceride formation are provided below (all in % area on GC chromatogram).

Uncoated Millicapsule: Glycerides Value

| Storage condition | Initial | 1 month | 3 month | 6 month | 9 month | 12 month |
| --- | --- | --- | --- | --- | --- | --- |
| 25° C./60% RH | 0.5% | 0.7% | 1.0% | 1.0% | 1.3% | 1.3% |
| 40° C./75% RH | 0.5% | 0.8% | 1.6% | 2.6% | Not tested | Not tested |

Coated Millicapsule (Coat #1): Glycerides Value

| Storage condition | Initial | 1 month | 3 month | 6 month | 9 month | 12 month |
| --- | --- | --- | --- | --- | --- | --- |
| 25° C./60% RH | 0.6% | 0.6% | 0.9% | 1.0% | 1.4% | 1.3% |
| 40° C./75% RH | 0.6% | 0.7% | 1.9% | 2.4% | Not tested | Not tested |

By comparison, the Epanova 1 g capsules have demonstrated the following glyceride formation in similar stability studies, packaged in bottles (expected market packaging), where Batches A, B and C are not the same batches of PUFA composition as used in the clinical study described in Example 3.

| Batch | Condition | Initial (% a/a)* | 3 month (% a/a) | 6 month (% a/a) | 9 month (% a/a) | 12 month (% a/a) |
| --- | --- | --- | --- | --- | --- | --- |
| A | 25° C./60% RH | 0.6 | 1.8 | 2.3 | 3.8 | 3.3 |
| A | 40° C./75% RH | 0.6 | 4.4 | 8.1 | Not tested | Not tested |
| B | 25° C./60% RH | <0.1 | 1.6 | 2.0 | 2.6 | 3.4 |
| B | 40° C./75% RH | <0.1 | 5.8 | 9.8 | Not tested | Not tested |
| C | 25° C./60% RH | <0.1 | 1.7 | 1.3 | 2.0 | 3.6 |
| C | 40° C./75% RH | <0.1 | 4.2 | 7.7 | Not tested | Not tested |

*% a/a is area percent on GC chromatogram.

These data demonstrate the reduced glyceride formation of the millicapsules in the aluminium sachet packaging.

EQUIVALENTS AND INCORPORATION BY REFERENCE

All publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that various changes can be made without departing from the spirit and scope of the claimed invention(s).

We claim:

1. A millicapsule formulation containing a plurality of seamless millicapsules, the millicapsules containing a polyunsaturated fatty acid (PUFA) composition,
   wherein the PUFA composition comprises:
   EPA, substantially in free acid form, in an amount of 50 wt % to 60 wt %,
   DHA, substantially in free acid form, in an amount of 15 wt % to 25 wt % and
   DPA, substantially in free acid form, in an amount of 1 wt % to 8 wt %,
   wherein the millicapsules are soft gelatin capsules comprising porcine Type A gelatin,
   wherein the millicapsules are approximately spherical in shape and include a diameter of about 4 mm,
   wherein the plurality of the millicapsules comprise about 1500 mg to about 2500 mg of the PUFA composition, and
   wherein the plurality of the millicapsules are about 40 to about 200 millicapsules.

2. The millicapsule formulation of claim 1, wherein the PUFA composition comprises:
   EPA, substantially in free acid form, in an amount of 50 wt % to 60 wt %,
   DHA, substantially in free acid form, in an amount of 17 wt % to 23 wt % and
   DPA, substantially in free acid form, in an amount of 1 wt % to 8 wt %,
   wherein at least 90% by weight of the polyunsaturated fatty acids in the composition are present in free acid form.

3. The millicapsule formulation of claim 1, wherein the plurality of the millicapsules comprise about 2000 mg of the PUFA composition.

4. The millicapsule formulation of claim 1, wherein the plurality of the millicapsules are about 80 millicapsules.

5. The millicapsule formulation of claim 1, wherein the millicapsules are uncoated.

6. The millicapsule formulation of claim 1, wherein the millicapsules are coated.

7. The millicapsule formulation of claim 6, wherein the millicapsules are coated with a coating comprising a poly (ethylacrylate-methylmethacrylate) 2:1 copolymer.

8. The millicapsule formulation of claim 7, wherein the millicapsules have a weight ratio of PUFA composition to coating of about 10:1 to about 25:1.

9. The millicapsule formulation of claim 7, wherein the millicapsules have a weight ratio of PUFA composition to coating of about 25:1 to about 50:1.

10. The millicapsule formulation of claim 1, wherein each millicapsule contains about 15 to about 50 mg of the PUFA composition.

11. The millicapsule formulation of claim 1 wherein the plurality of the millicapsules are present in a sachet, a packet, a stick-pack or a blister in a blister pack.

12. The millicapsule formulation of claim 1, comprising:
about 80 seamless, approximately spherical soft gelatin millicapsules each with a diameter of about 4 mm and comprising porcine Type A gelatin,
wherein the millicapsules contain a total of about 2000 mg of a polyunsaturated fatty acid (PUFA) composition,
wherein the PUFA composition comprises:
EPA, substantially in free acid form, in an amount of 50 wt % to 60 wt %,
DHA, substantially in free acid form, in an amount of 15 wt % to 25 wt % and
DPA, substantially in free acid form, in an amount of 1 wt % to 8 wt %, and
wherein the millicapsules are coated, the coating being made from a total of 1.6 mg of sodium carboxymethylcellulose, 1.0 mg of yellow iron oxide, 90 mg of talc, 18 mg of titanium dioxide, 1.6 mg of polysorbate 80, 52 mg of a poly(ethylacrylate-methylmethacrylate) 2:1 copolymer mixed with polyethylene glycol octadecyl ether and water.

13. A method of treating severe hypertriglyceridemia comprising administering to a patient in need thereof the millicapsule formulation of claim 1 in an amount and for a duration sufficient to treat the severe hypertriglyceridemia.

14. A method of treating mixed dyslipidemia comprising administering to a patient in need thereof the millicapsule formulation of claim 1 in an amount and for a duration sufficient to treat the mixed dyslipidemia.

15. A method of treating cystic fibrosis comprising administering to a patient in need thereof the millicapsule formulation of claim 1 in an amount and for a duration sufficient to the treat cystic fibrosis.

16. A method of treating NASH comprising administering to a patient in need thereof the millicapsule formulation of claim 1 in an amount and for a duration sufficient to treat the NASH.

17. A method of treating hyperlipoproteinemia comprising administering to a patient in need thereof the millicapsule formulation of claim 1 in an amount and for a duration sufficient to treat the hyperlipoproteinemia.

18. The millicapsule formulation of claim 1, wherein the PUFA compostion comprises:
EPA, substantially in free acid form, in an amount of 50 wt % to 60 wt %,
DHA, substantially in free acid form, in an amount of 17 wt % to 23 wt % and
DPA, substantially in free acid form, in an amount of 1 wt % to 8 wt %.

19. The millicapsule formulation of claim 11 wherein the plurality of the millicapsules are present in a sachet.

20. The millicapsule formulation of claim 19 wherein the sachet is an aluminum sachet.

21. The millicapsule formulation of claim 1, wherein the gelatin has a bloom strength of 200±10%.

22. The method of claim 15, wherein the patient is a pediatric patient.

* * * * *